United States Patent
Takaishi

(10) Patent No.: US 11,291,593 B2
(45) Date of Patent: Apr. 5, 2022

(54) UNDERPANTS-TYPE DISPOSABLE DIAPER

(71) Applicant: Daio Paper Corporation, Ehime (JP)

(72) Inventor: Mina Takaishi, Tochigi (JP)

(73) Assignee: Daio Paper Corporation, Ehime (JP)

( * ) Notice: Subject to any disclaimer, the term of this patent is extended or adjusted under 35 U.S.C. 154(b) by 638 days.

(21) Appl. No.: 16/303,279

(22) PCT Filed: May 30, 2017

(86) PCT No.: PCT/JP2017/019999
§ 371 (c)(1),
(2) Date: Nov. 20, 2018

(87) PCT Pub. No.: WO2017/221640
PCT Pub. Date: Dec. 28, 2017

(65) Prior Publication Data
US 2019/0209393 A1    Jul. 11, 2019

(30) Foreign Application Priority Data
Jun. 20, 2016   (JP) .............................. JP2016-122084

(51) Int. Cl.
*A61F 13/494*   (2006.01)
*A61F 13/496*   (2006.01)
(Continued)

(52) U.S. Cl.
CPC ............ *A61F 13/496* (2013.01); *A61F 13/49* (2013.01); *A61F 13/494* (2013.01);
(Continued)

(58) Field of Classification Search
CPC .......... A61F 13/49406; A61F 13/49413; A61F 13/4942; A61F 13/496; A61F 2013/15243;
(Continued)

(56) References Cited

U.S. PATENT DOCUMENTS 6,506,187 B1 *   1/2003   Andersson ........ A61F 13/49413
                                                604/385.01
7,318,820 B2 *   1/2008   LaVon .............. A61F 13/49413
                                                604/385.24
(Continued)

FOREIGN PATENT DOCUMENTS

CN    208031383     11/2018
JP    2002159529 A   6/2002
(Continued)

OTHER PUBLICATIONS

International Search Report for PCT/JP2017/019999, dated Aug. 15, 2017.

*Primary Examiner* — Catharine L Anderson
(74) *Attorney, Agent, or Firm* — Andrus Intellectual Property Law, LLP

(57) ABSTRACT

In an underpants-type disposable diaper, three-dimensional gathers are provided on both sides in the width direction of an inner member. A fallen portion of each of the three-dimensional gather has a fallen non-stretchable portion to which a contraction force of gather elastic members does not act. A character representation is printed at a position in the fallen non-stretchable portion of the inner member, and this character representation is made visible from the inside of the diaper.

9 Claims, 23 Drawing Sheets

(51) Int. Cl.
*A61F 13/49* (2006.01)
*A61F 13/511* (2006.01)
*A61F 13/514* (2006.01)
*A61F 13/53* (2006.01)
*A61F 13/84* (2006.01)

(52) U.S. Cl.
CPC ...... *A61F 13/49413* (2013.01); *A61F 13/511* (2013.01); *A61F 13/514* (2013.01); *A61F 13/53* (2013.01); *A61F 2013/8497* (2013.01)

(58) Field of Classification Search
CPC .......... A61F 2013/49092; A61F 2013/494633; A61F 2013/8497
See application file for complete search history.

(56) References Cited

U.S. PATENT DOCUMENTS

| | | | | |
|---|---|---|---|---|
| 7,432,412 B2* | 10/2008 | Kigata | ................ | A61F 13/4751 604/361 |
| 7,632,257 B2* | 12/2009 | Magee | ................... | A61F 13/84 604/385.01 |
| 7,766,889 B2* | 8/2010 | Erdman | ............ | A61F 13/49014 604/385.26 |
| 7,824,385 B2* | 11/2010 | Ecker | ................... | A61F 13/4758 604/385.01 |
| 7,959,620 B2* | 6/2011 | Miura | ............... | A61F 13/51394 604/385.02 |
| 8,563,802 B2* | 10/2013 | Nishikawa | ............ | A61F 13/511 604/361 |
| 8,946,500 B2* | 2/2015 | Hopkins | ............. | A61F 13/4758 604/361 |
| 9,072,631 B2* | 7/2015 | Nakajima | ......... | A61F 13/47263 |
| 2019/0209393 A1 | 7/2019 | Takaishi | | |

FOREIGN PATENT DOCUMENTS

| | | |
|---|---|---|
| JP | 2004254861 A | 9/2004 |
| JP | 2005237768 A | 9/2005 |
| JP | 2006181192 A | 7/2006 |
| JP | 2007-097619 | 4/2007 |
| JP | 2008307298 A | 12/2008 |
| JP | 2012-143469 | 8/2012 |
| JP | 2012245133 A | 12/2012 |
| JP | 2013198651 A | 10/2013 |
| JP | 2014-198136 | 10/2014 |
| JP | 2017225507 | 12/2017 |

* cited by examiner (a)

(b)

(c)

(a)

(b)

(c)

(a)

(b)

UNDERPANTS-TYPE DISPOSABLE DIAPER

CROSS-REFERENCE TO RELATED APPLICATIONS

This application is the U.S. national stage application of International Application PCT/JP2017/019999, filed May 30, 2017, which international application was published on Dec. 28, 2017, as International Publication WO 2017/221640 in the Japanese language. The International Application claims priority of Japanese Patent Application No. 2016-122084, filed Jun. 20, 2016. The international application and Japanese application are both incorporated herein by reference, in entirety.

TECHNICAL FIELD

The present invention relates to an underpants-type disposable diaper having a character representation.

BACKGROUND ART

An underpants-type disposable diaper is known in which product management characters necessary for product management such as a product lot number in addition to confirmation letters at the time of use for a user indicating size and front and back directions are printed (for example, refer to Patent Literatures 1 and 2).

However, as in the conventional underpants-type disposable diaper, when the character representation is provided on an outer member, since fine wrinkles and pleats are formed in a stretchable region of the outer member, and there is a problem that visibility of the character representation deteriorates. Considering from the viewpoint of a wearer, when a user uses an underpants-type disposable diaper by hand, an area of the outer member that is easily visible is a lower torso portion, but in recent underpants-type disposable diapers, to ensure fitting, substantially the entire lower torso portion of an outer member is a stretchable region, and deterioration of visibility due to wrinkles and pleats cannot be avoided.

CITATION LIST

Patent Literature

Patent Literature 1: JP 2012-245133 A
Patent Literature 2: JP 2005-237768 A

SUMMARY OF THE INVENTION

Technical Problem

It is therefore an object of the present invention to provide an underpants-type disposable diaper having a character representation which is easy to see at the time of wearing and is also excellent in visibility of characters.

Solution to Problem

The representative aspects of the present invention that have solved the above problems will be described below.
<First Aspect>
An underpants-type disposable diaper comprising: an outer member, which is extending from a front body to a back body as one unit, or outer members, which are separately provided on the front body and the back body; an inner member, which has a liquid pervious top sheet positioned on a front surface side, a liquid impervious sheet positioned on a back surface side, and an absorber interposed therebetween, which extends in the front-back direction from the front body to the back body, and which is joined to the outer member; and
three-dimensional gathers, which are provided on both sides in the width direction of the inner member,
wherein each of the three-dimensional gathers includes a main unit section positioned on each of both side portions of the inner member, fallen portions located on the front and back end portions of the main unit section and fixed in a fallen state, a non-fixed free portion located between the fallen portions in the main unit section, and a gather elastic member attached to the free portion, such that the free portion stands up by a contraction force of the gather elastic member,
the fallen portion has a fallen non-stretchable portion to which the contraction force of the gather elastic member does not act, and
a character representation is printed at a position in the fallen non-stretchable portion of the inner member, and the character representation is made visible on the inside of the diaper.
(Function and Effect)
The present invention is characterized in that a character representation is printed at the position in the fallen non-stretchable portion of the three-dimensional gather in the inner member. Although the fallen portion of the three-dimensional gather is located inside the diaper, the fallen portion can be seen through a waist opening when a wearer passes the leg through a leg opening and is easily visible. Moreover, the character representation does not impair the aesthetic appearance of external appearance. In addition, since the fallen non-stretchable portion is the non-stretchable portion, deterioration of the visibility of the character representation due to contraction wrinkles and pleats of the fallen non-stretchable portion itself hardly occurs.
<Second Aspect>
The underpants-type disposable diaper according to the first aspect,
wherein, in the fallen non-stretchable portion, a surface layer located on the most front surface side is not fixed to a layer adjacent to a back surface side of the surface layer, and the character representation is printed on the surface layer.
(Function and Effect)
In this manner, if the character representation is printed on the surface layer which is located on the most front surface side in the fallen non-stretchable portion and is not fixed to the member adjacent to the back surface side of the surface layer, deformation such as contraction of the member positioned on the back surface side of the surface layer is less likely to influence to the surface layer, and it is possible to effectively prevent deterioration of visibility due to deformation of the character representation.
<Third Aspect>
The underpants-type disposable diaper according to the first or second aspect,
wherein the outer member has a stretchable region, which is stretchable in the width direction, at a position corresponding to the character representation in the front-back direction, and
each of both side portions of the inner member in the width direction including at least a part of the character representation is not joined to the outer member.
(Function and Effect)
When the inner member is joined to the stretchable region of the outer member, the inner member is influenced by contraction of the outer member. In this case, although deterioration of visibility of the character representation is less than in the case where the character representation is provided on the outer member, deterioration of visibility due to deformation of the character representation cannot be avoided. To solve this, as described above, the structure in which each of both the side portions in the width direction including at least a part of the character representation on the inner member is not joined to the outer member is preferable since the contraction of the outer member is unlikely to influence to the character representation in the inner member.

<Fourth Aspect>

The underpants-type disposable diaper according to any one of the first to third aspects, wherein the absorber extends in the front-back direction so as not to reach a position of the fallen portion at a front side and a position of the fallen portion at a back side, the liquid impervious sheet extends in the front-back direction so as to reach the position of the fallen portion at the front side and the position of the fallen portion at the back side, and the liquid impervious sheet is provided so as to include at least a position of the character representation in the fallen portion.

(Function and Effect)

Since the fallen portions of the three-dimensional gather have almost no leakage prevention function, it is desirable to provide the fallen portions at the front end back end portions without the absorber. However, if the absorber is not present at the positions of the fallen portions, the rigidity is lowered such that the fallen portions are likely to be deformed, and when the character representation of the fallen non-stretchable portion is deformed, visibility of the character representation may be deteriorated. To solve this, if the liquid impervious sheet is extended in the front-back direction so as to reach the position of the fallen portion at the front side and the position of the fallen portion at the back side, and the liquid impervious sheet is provided so as to include at least a position of the character representation in the fallen portion, the fallen non-stretchable portion is unlikely to be deformed due to the rigidity of the liquid impervious sheet, and it is possible to prevent deterioration of visibility of the character representation.

<Fifth Aspect>

The underpants-type disposable diaper according to any one of the first to fourth aspects, wherein the character representation is printed on a front surface of the fallen non-stretchable portion.

(Function and Effect)

It is preferable that the character representation is printed on the front surface of the fallen non-stretchable portion, since it is most easily visible.

<Sixth Aspect>

The underpants-type disposable diaper according to any one of the first to fourth aspects, wherein the character representation is printed on a surface located on a back surface side of a front surface of the fallen non-stretchable portion.

(Function and Effect)

It is preferable that the character representation is printed, not on the front surface of the fallen non-stretchable portion, but on the surface located on the back surface side of the front surface, since the printed portion does not directly touch the skin.

Advantage Effects of Invention

As described above, according to the present invention, there is an advantage that an underpants-type disposable diaper having a character representation which is easy to see at the time of wearing and is also excellent in visibility of characters is provided and so on.

DESCRIPTION OF EMBODIMENTS

Figure 1:
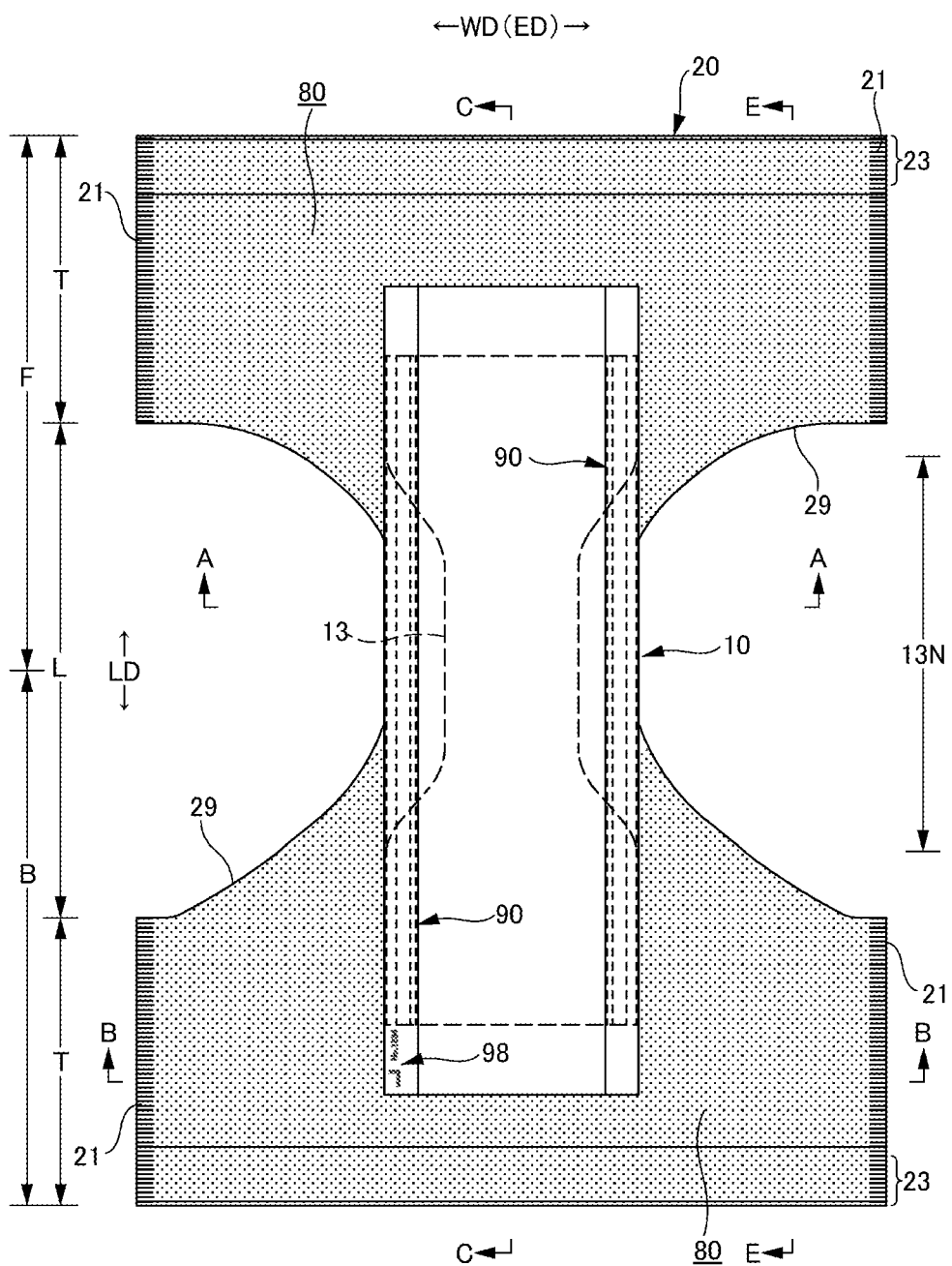
FIG. 1 is a plan view (inner surface side) of an underpants-type disposable diaper in a spread state.

Hereinafter, embodiments of the present invention will be described in detail with reference to the accompanying drawings. In addition, a dotted portion in the cross sectional view indicates a joining means such as a hot melt adhesive.

FIGS. 1 to 6 illustrate an underpants-type disposable diaper. This underpants-type disposable diaper (hereinafter also simply referred to as a diaper) has an outer member 20 disposed in a front body F and a back body B, and an inner member 10 fixed, as one unit, to an inner surface of the outer member 20, and the inner member 10 is formed by interposing an absorber 13 between a liquid pervious top sheet 11 and a liquid impervious sheet 12. Upon manufacturing, after a back surface of the inner member 10 is joined to an inner surface (upper surface) of the outer member 20 by a joining means such as a hot melt adhesive, the inner member 10 and the outer member 20 are folded at the center in the front-back direction LD (longitudinal direction) which is a boundary between the front body F and the back body B, and both side portions thereof are joined to each other by thermal welding, a hot melt adhesive, or the like to form a side seal portion 21. As a result, an underpants-type disposable diaper having a waist opening and a pair of left and right leg openings can be formed.

(Structure Example of Inner Member)

Figure 4:
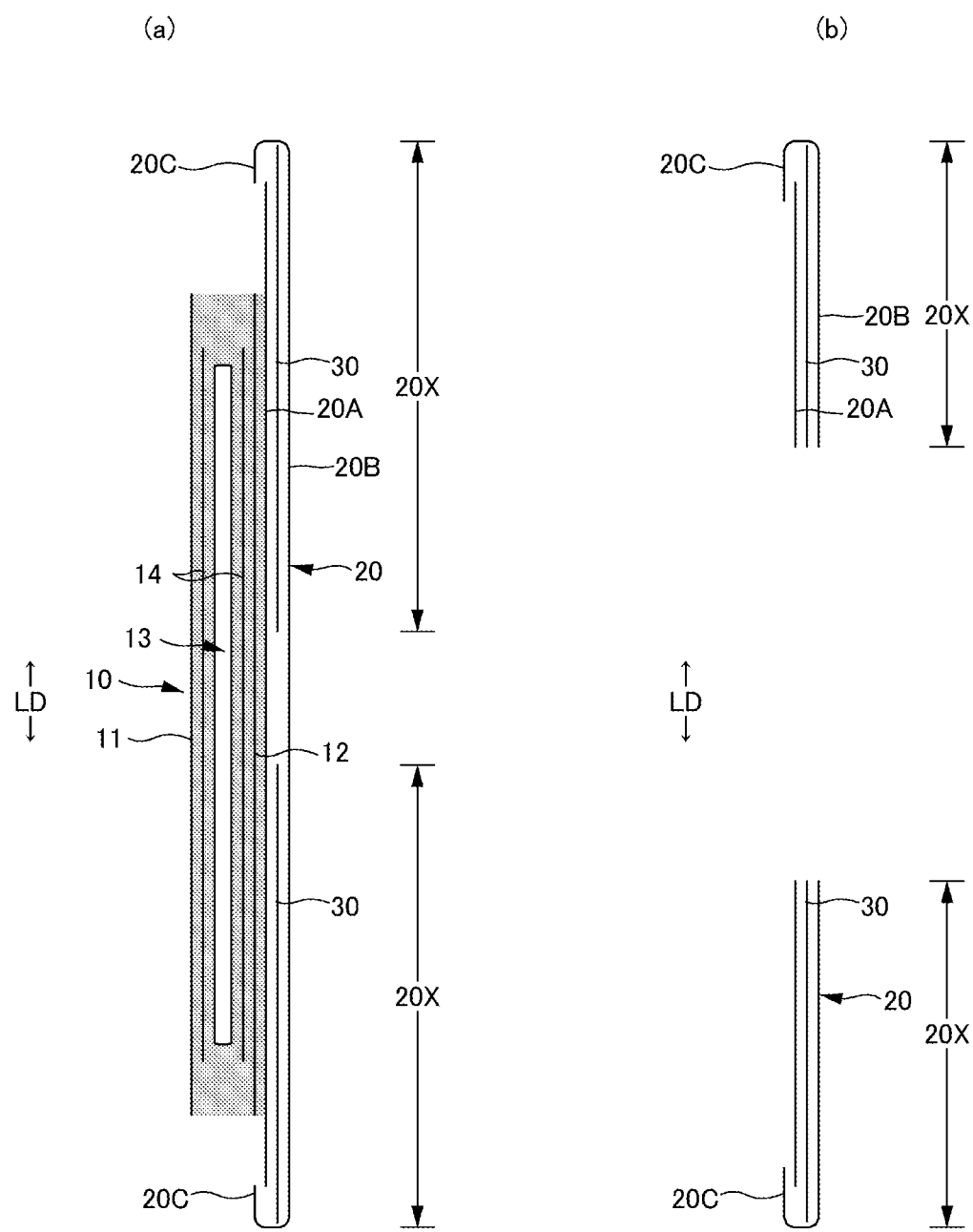
FIG. 4(a) is a cross sectional view taken along line C-C of FIG. 1.
FIG. 4(b) is a cross sectional view taken along line E-E of FIG. 1.
Figure 5:
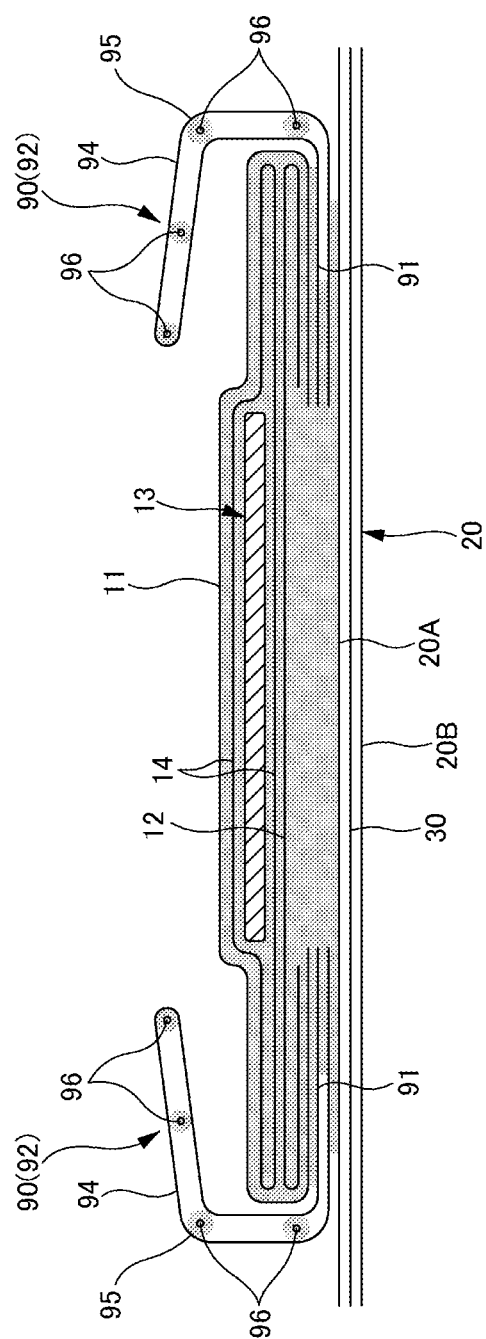
FIG. 5 is a cross-sectional view taken along line A-A of FIG. 1.
Figure 6:
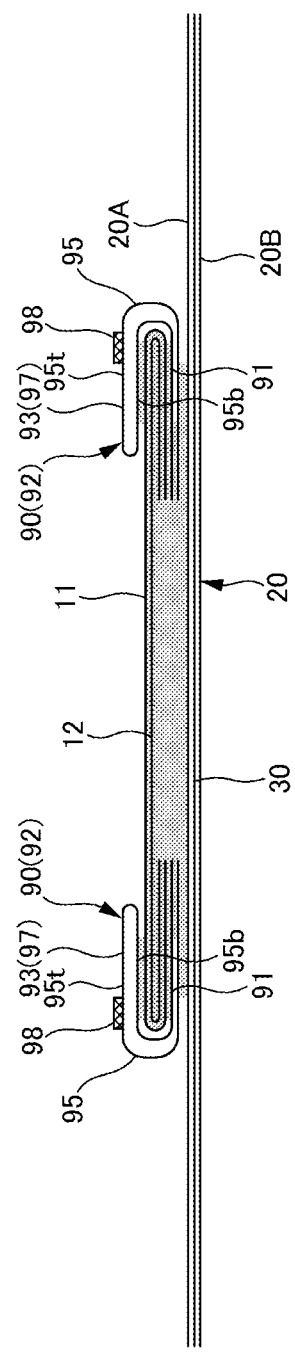
FIG. 6 is a cross-sectional view taken along line B-B of FIG. 1.

As illustrated in FIGS. 4 to 6, the inner member 10 has a structure in which the absorber 13 is interposed between the liquid pervious top sheet 11 and the liquid impervious sheet 12 made of polyethylene or the like to absorb and retain excreted fluid that has permeated through the liquid pervious top sheet 11. The planar shape of the inner member 10 is not particularly limited, but generally, it is a substantially rectangular shape as illustrated in FIG. 1.

As the liquid pervious top sheet 11 covering a front surface side (skin side) of the absorber 13, a perforate or non-perforate nonwoven fabric, a porous plastic sheet, or the like is suitably used. For a raw material fiber forming a nonwoven fabric, in addition to synthetic fibers such as olefin type such as polyethylene or polypropylene, polyester type, polyamide type, etc., regenerated fibers such as rayon and cupra, and natural fibers such as cotton can be used, and a nonwoven fabric obtained by an appropriate processing method, such as a spun lace method, a spun bond method, a thermal bond method, an melt blown method, and a needle punch method can be used. In these processing methods, the spun lace method is excellent in terms of flexibility and drapability, and the thermal bond method is excellent in terms of bulkiness and softness. When a large number of through holes are formed on the liquid pervious top sheet 11, urine and the like are quickly absorbed, and dry touch property is excellent. The liquid pervious top sheet 11 extends to back surface sides of the absorber 13 by wrapping up side edge portions of the absorber 13.

For the liquid impervious sheet 12 covering a back surface side (non-skin contact side) of the absorber 13, a liquid impermeable plastic sheet such as polyethylene or polypropylene is used. In recent years, those having moisture permeability are preferably used from the viewpoint of prevention of stuffiness. This waterproof/moisture pervious sheet is a microporous sheet obtained by stretching a sheet in one or two axial directions after forming the sheet by weld kneading an inorganic filler in an olefinic resin such as polyethylene and polypropylene.

The absorber 13 is basically a known absorber, for example, an accumulated body of pulp fibers, assembly of filaments such as cellulose acetate, or nonwoven fabrics, and as necessary, a super absorbent polymer can be mixed and fixed. The absorber 13 can be wrapped with a package sheet 14 having liquid permeability and liquid retention, such as crepe paper, as necessary, for shape and polymer retention and the like.

The shape of the absorber 13 is formed in a substantially hourglass shape having a narrowing portion 13N narrower than the front and back sides at a crotch portion. Although the size of the narrowing portion 13N can be determined as appropriate, the length in the front-back direction of the narrowing portion 13N can be set to about 20 to 50% of the maximum length of the diaper, and the width of the narrowest portion is about 40 to 60% of the maximum width of the absorber 13. In the case where such the narrowing portion 13N is provided, if the planar shape of the inner member 10 is substantially rectangular, non-absorber side portions 17 without the absorber 13 are formed due to the narrowing portion 13N of the absorber 13 in the inner member 10.

The liquid impervious sheet 12 is folded back to the back surface side together with the liquid pervious top sheet 11 on both sides in the width direction of the absorber 13. As this liquid impervious sheet 12, it is desirable to use an opaque sheet such that brown color of defecation, urine, and the like does not appear. As the opacification, a film obtained by internally adding a pigment or a filler such as calcium carbonate, titanium oxide, zinc oxide, white carbon, clay, talc, barium sulfate, or the like in a plastic is suitably used.

Three-dimensional gathers 90 fitting around the legs are formed on both sides of the inner member 10. As illustrated in FIGS. 5 and 6, the three-dimensional gather 90 includes a fixed portion 91, a main unit section 92, a fallen portion 93, and a free portion 94. The fixed portion 91 is fixed to a side portion of a back surface of the inner member 10. The main unit section 92 extends from the fixed portion 91 through a side of the inner member 10 to above a side portion of a front surface of the inner member 10. The fallen portions 93 are formed by fixing the front and back end portions of the main unit section 92 to the side portion of the surface (the liquid pervious top sheet 11 in the illustrated embodiment) of the inner member 10 in a fallen state. The free portion 94 is formed between the fallen portions 93 by being unfixed. Each of these portions is formed by a gather sheet 95 formed by folding a sheet such as a nonwoven fabric into a double sheet. The gather sheet 95 is attached to the entire front-back direction of the inner member 10, the fallen portions 93 are provided on a front side and a back side of the non-absorber side portion 17, and the free portion 94 extends on both front and back sides of the non-absorber side portion 17. Further, between the double gather sheets 95, elongated gather elastic members 96 are disposed at a tip portion of the free portion and the like. As illustrated in FIG. 5, in a product state, the gather elastic members 96 are provided for making the free portion 94 stand up by an elastic contraction force.

In the three-dimensional gather 90 illustrated in FIGS. 5 and 6, the main unit section 92 is not folded back. However, any known structures can be used as long as a character representation 98 can be provided on a fallen non-stretchable portion 97 to be described later, such as a structure in which, a portion on a root side of the main unit section 92 obliquely stands toward the center in the width direction, and a portion on a tip side of the intermediate portion obliquely stands outward in the width direction.

As the gather elastic member 96, materials such as styrene rubber, olefin rubber, urethane rubber, ester rubber, polyurethane, polyethylene, polystyrene, styrene butadiene, silicone, polyester, and the like which are usually used can be used. Further, in order to make it difficult to be seen from the outside, it is better that the thickness is set to 925 dtex or less, the tension is set to 150 to 350%, and the interval is set to 7.0 mm or less. As the gather elastic member 96, in addition to a thread-like shape as the illustrated embodiment, a tape-shaped member having a certain width can be used.

Like the liquid pervious top sheet 11, for a material fiber forming the above-described gather sheet 95, in addition to synthetic fibers such as olefin type such as polyethylene or polypropylene, polyester type, amide type, etc., regenerated fibers such as rayon and cupra, and natural fibers such as cotton can be used, and a nonwoven fabric obtained by an appropriate processing method, such as a spun bond method, a thermal bond method, an melt blown method, and a needle punch method can be used. In particular, to prevent stuffiness, nonwoven fabric having low basis weight and excellent in air permeability is preferably used. Further, with respect to the gather sheet 95, in order to prevent permeation of urine or the like and also to prevent rash and improve the texture to the skin (dry touch), it is desirable to use a water repellent treated nonwoven fabric coated with silicone type, paraffin metal type, or alkylchromic chloride type water repellent, etc.

Figure 14:
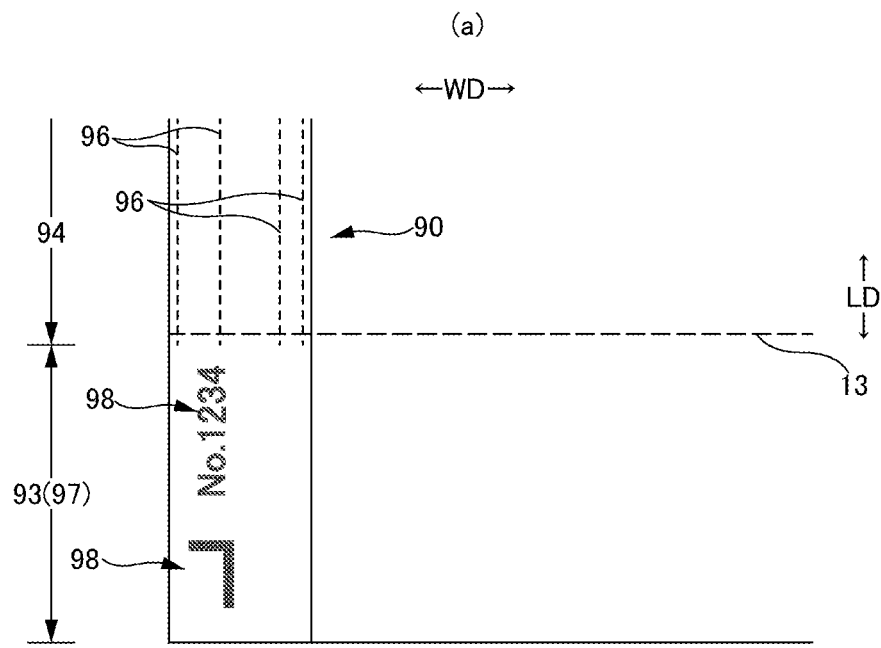
FIG. 14 is an enlarged plan view of a main part including a fallen portion.
Figure 14:
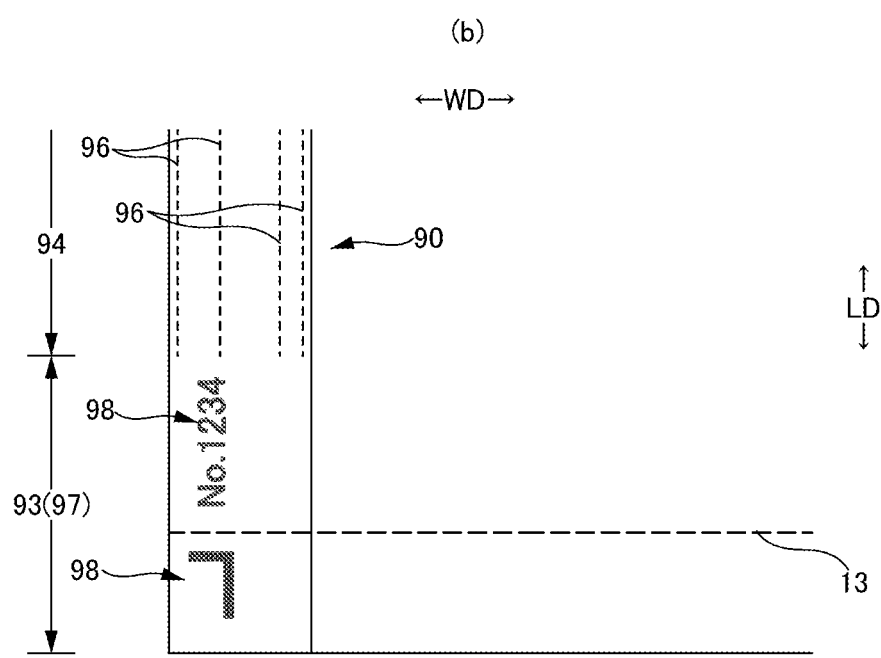

Characteristically, as illustrated in FIG. 14, the fallen portion 93 of the three-dimensional gather 90 has the fallen non-stretchable portion 97 on which a contraction force of the gather elastic member 96 does not act, and the character representation 98 is printed at a position in the fallen non-stretchable portion 97 of the inner member 10, and this character representation 98 is visible on the inside of a diaper. Although the fallen portion 93 of the three-dimensional gather 90 is located inside the diaper, it is a part that can be seen through a waist opening when a wearer passes the leg through a leg opening and is a part that is easily visible. Moreover, the character representation 98 does not impair the aesthetic appearance of external appearance. In addition, since the fallen non-stretchable portion 97 is non-stretchable, the visibility of the character representation 98 is hardly deteriorated due to contraction wrinkles and pleats of the fallen non-stretchable portion itself.

Characters of the character representation 98 are not particularly limited, but rather than those unrelated to use such as a manufacturer's name, a distributor's name, a product name etc., those for a user's confirmation at the time of use like letters such as "S", "M", "L", etc. indicating the size; "front", "back", etc. indicating which side it is front, back, etc., are particularly suitable. Further, when the character representation e.g. a product lot number is represented on an outer surface of a product, the aesthetic appearance is impaired, but for such a product management letter which is necessary for the product management, the character representation 98 of the present application is suitable.

The fallen portion 93 may have a plurality of the character representations 98. In that case, although it is desirable that all character representations 98 be represented at positions in the fallen non-stretchable portion 97 as the illustrated embodiment, as long as at least one of the character representations 98 is entirely represented at the position in the fallen non-stretchable portion 97, each of remaining character representations 98 may be entirely or partly located outside the fallen non-stretchable portion 97.

It is preferable that the fallen non-stretchable portion 97 be the whole of the fallen portion 93, but a part of the fallen portion 93 may have stretchability. For example, the end portion of the fallen portion 93 on the side of the free portion 94 may have stretchability, and the remaining portion may be the fallen non-stretchable portion 97. In order to make the fallen non-stretchable portion 97 non-stretchable, it is possible to adopt a structure without any gather elastic member 96. However, other structures also can be adopted, in which, although an end portion of each gather elastic member 96 is positioned on the fallen non-stretchable portion 97, this end portion of the gather elastic member 96 is unfixed to the fallen non-stretchable portion 97 so as to be the free portion 94; this end portion is fixed to the fallen non-stretchable portion 97 in a non-stretching state; or stretchability is substantially killed by cutting the gather elastic member finely. In the structure illustrated in FIGS. 5 and 6, in a portion other than the fallen non-stretchable portions 97, the gather elastic members 96 are adhered and fixed to the gather sheet 95 with a hot melt adhesive at positions of the gather elastic members 96, and opposing surfaces of the gather sheet 95 are joined. On the other hand, in the fallen non-stretchable portion 97, no hot melt adhesive is provided at the positions of the gather elastic members 96, and therefore, the gather elastic members 96 and the gather sheet 95 are not adhered, and opposing surfaces of the gather sheet 95 are not joined at the positions having the gather elastic members 96.

Although the dimensions of the fallen non-stretchable portion 97 can be appropriately determined, it is desirable that the width be about 10 to 30 mm, and the length in the front-back direction be about 50 to 80 mm. The size of the character representation 98 is preferably five points or larger, particularly about five to twenty four points.

Figure 22:
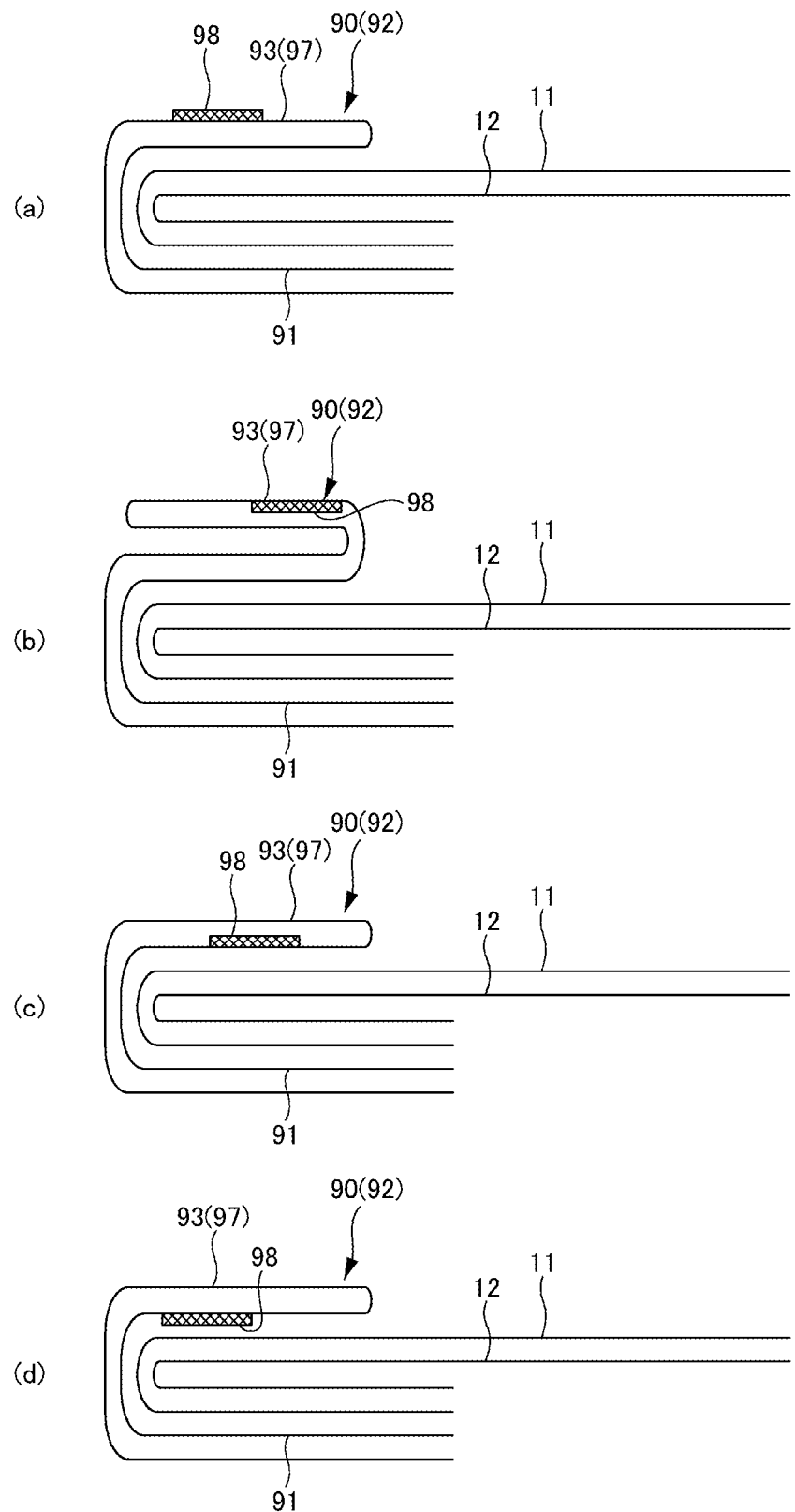
FIG. 22 is an enlarged sectional view of a main part including a fallen portion.
Figure 23:
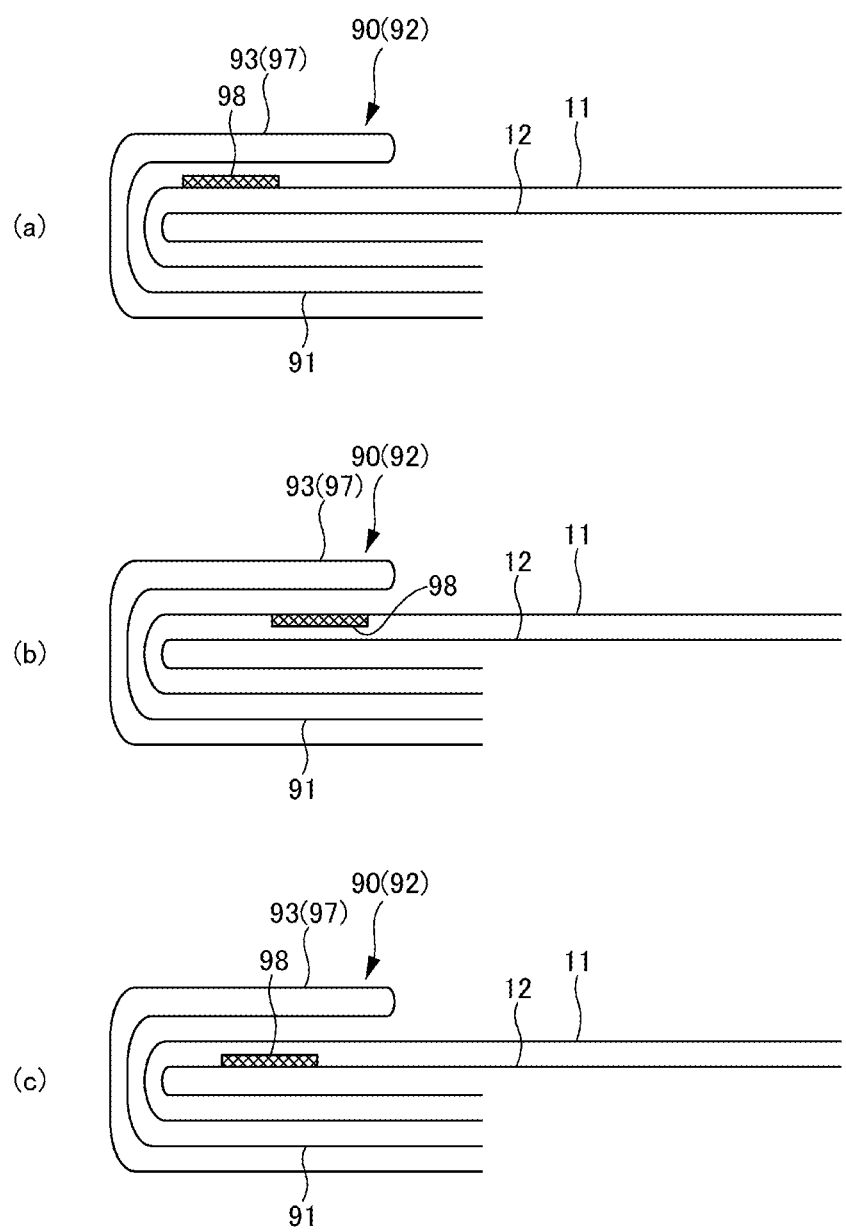
FIG. 23 is an enlarged cross-sectional view of a main part including a fallen portion.

The position of the character representation 98 is not particularly limited as long as the position is in the fallen non-stretchable portion 97, and the character representation 98 can be printed on a surface located on the back surface side of the surface of the fallen non-stretchable portion 97 as illustrated in FIGS. 22(b) to 22(d), and 23 in addition to printing on the surface of the fallen non-stretchable portion 97 as illustrated in FIG. 22(a). This embodiment is preferable since it is most easily visible, and the other embodiments are preferable since the printed portions do not directly touch the skin. More specifically, in the embodiment illustrated in FIG. 22(a), the character representation 98 is printed on a surface of the portion located on the most front surface side of the gather sheet 95, in the embodiments illustrated in FIGS. 22(b) and 22(c), the character representation 98 of each embodiment is printed on a surface of opposing surfaces ((b) a surface located on the front surface side, and (c) a surface located on the back surface side) of two-layered structure formed by folding back the gather sheet 95, and in the embodiment illustrated in FIG. 22(d), the character representation 98 is printed on the a surface of the gather sheet 95 facing the liquid pervious top sheet 11. Further, in the embodiment illustrated in FIG. 23(a), the character representation 98 is printed on a surface (surface opposing the gather sheet 95) of the liquid pervious top sheet 11. In the embodiment illustrated in FIG. 23(b), the character representation 98 is printed on a back surface (surface opposing the liquid impervious sheet 12) of the liquid pervious top sheet 11. In the embodiment illustrated in FIG.

23(c), the character representation 98 is printed on a surface (surface opposing the liquid pervious top sheet 11) of the liquid impervious sheet 12. In the embodiment illustrated in FIG. 22(a), the printed portion can be visually recognized directly, while the other portions are seen through layers located on the front surface side.

As illustrated in FIG. 6, a surface layer 95t located on the most front surface side in the fallen non-stretchable portion 97 is not fixed to an adjacent layer 95b on the back surface side, and as illustrated in FIGS. 22(a) and 22(b), the embodiments in which the character representations 98 are printed on the surface layer 95t are preferred embodiments. As a result, deformation such as contraction of a member located on the back surface side of the surface layer 95t is less likely to influence to the surface layer 95t, and deterioration of visibility due to deformation of the character representation 98 can be therefore effectively prevented. In order to form such a structure, for example, as the illustrated embodiment, in the case of the two-layer structure formed by folding back the gather sheet 95, opposing surfaces of the gather sheet 95 are made not to join each other in the fallen non-stretchable portion 97.

As illustrated in FIG. 14(b), the fallen portions 93 of the three-dimensional gather 90 can be provided at positions in the front-back direction having the absorber 13, but since the fallen portions 93 have almost no leakage prevention function, it is desirable to provide the fallen portions 93 at the front and back end portions without the absorber 13 as illustrated in FIG. 14(a) and the like. However, if the absorber is not present in the fallen portion 93, the rigidity of the fallen portion 93 is lowered, and deformation is likely to occur, such that visibility of the character representation 98 may be deteriorated due to deformation of the character representation 98 of the fallen non-stretchable portion 97. To solve this, as the illustrated embodiment, the liquid impervious sheet 12 is extended in the front-back direction LD so as to reach the position of the fallen portion 93 at the front side and the position of the fallen portion 93 at the back side, and the liquid impervious sheet 12 is extended to at least the position of the character representation 98 of the fallen portion 93 in the width direction WD, the fallen non-stretchable portion 97 is unlikely to be deformed by the rigidity of the liquid impervious sheet 12. From this viewpoint, as the illustrated embodiment, it is further preferable that both the end portions in the width direction of the liquid impervious sheet 12 are folded back to form double structures. However, a rigidity improving effect can be sufficiently obtained even in a single structure in which both the end portions in the width direction of the liquid impervious sheet 12 are not folded back.

As illustrated in FIGS. 3 to 6, a back surface of the inner member 10 is joined to an inner surface of the outer member 20 with a hot melt adhesive or the like in the inner and outer joined region 10B (shaded region). The inner and outer joined region 10B can be determined appropriately and can be provided throughout almost the maximum width in the width direction WD of the inner member 10. However, it is preferable that the both side portions in the width direction of the inner and outer joined region are not fixed to the outer member 20 such that the inner and outer joined region 10B does not include at least a part of or preferably the whole of the character representation 98. That is, when the inner member 10 is joined to a stretchable region 80 of the outer member 20, contraction of the outer member 20 influences to the inner member 10, and although deterioration of visibility of the character representation 98 is less than in the case where the character representation 98 is provided on the outer member 20, deterioration of visibility due to deformation of the character representation 98 cannot be avoided. In order to solve this, as described above, a structure is preferable in which both the side portions in the width direction including at least a part of the character representation 98 on the inner member 10 are not joined to the outer member 20, since the contraction of the outer member 20 is unlikely to influence to the character representation 98 on the inner member 10.

(Structure Example of Outer Member)

Figure 7:
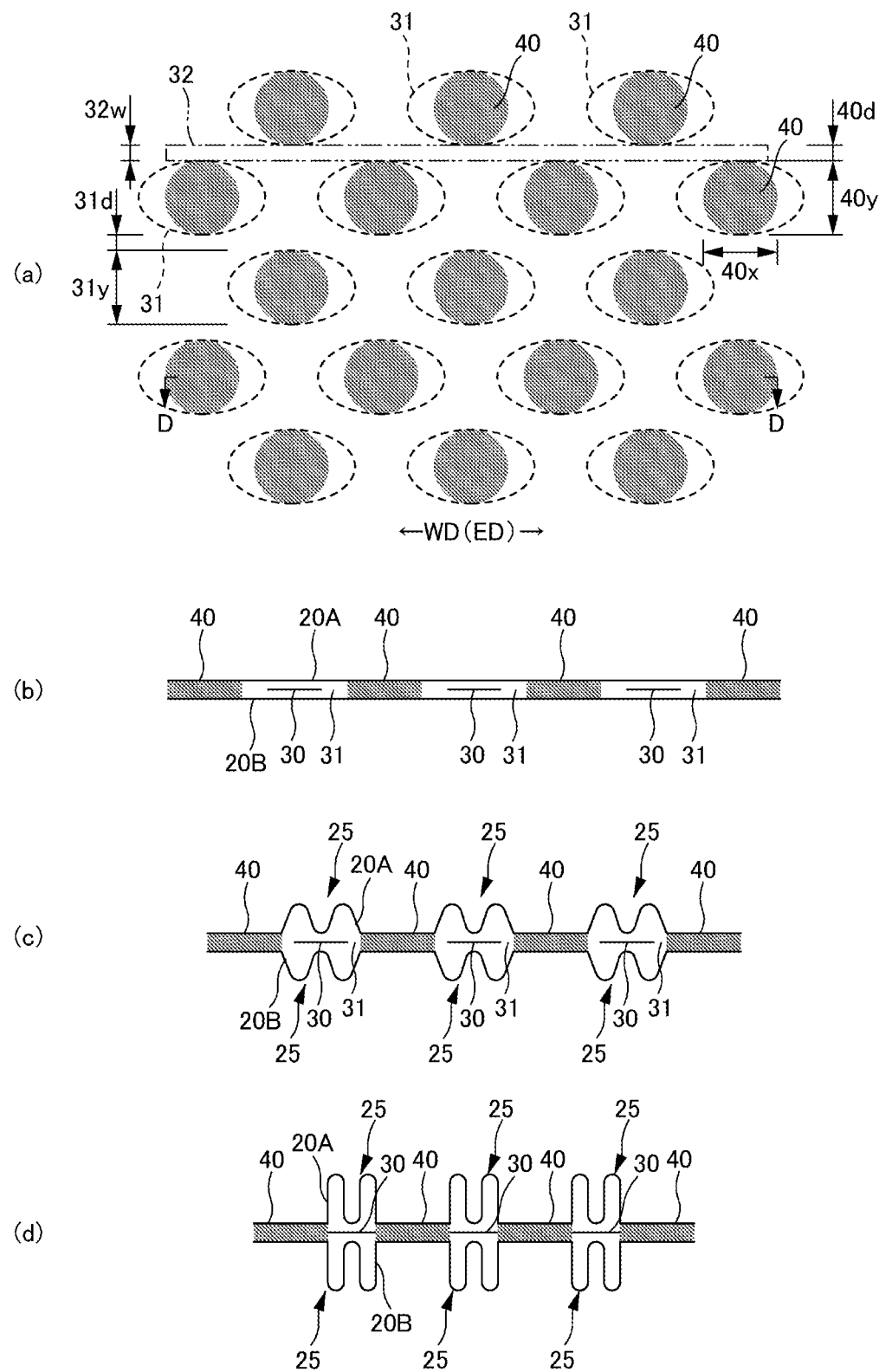
FIG. 7(a) is a plan view of a main part of a stretchable region.
FIG. 7(b) is a cross-sectional view taken along line D-D of FIG. 7(a)
FIG. 7(c) is a cross-sectional view in a worn state.
FIG. 7(d) is a cross-sectional view in a natural length state.

The outer member 20 extends from a side edge to a side of the absorber 13. In the crotch portion, the side edges of the outer member 20 may be located closer to the center side than the side edges of the inner member 10 in the width direction as in the illustrated embodiment, or may be located closer to the outer sides than the side edges of the inner member in the width direction. Further, the outer member 20 includes a lower torso portion T which is a range in the front-back direction corresponding to side seal portions 21 and an intermediate portion L which is a range in the front-back direction between the lower torso portion T of the front body F and the lower torso portion T of the back body B. In the outer member 20 of the illustrated embodiment, except for the middle in the front-back direction of the intermediate portion L, as illustrated in FIGS. 2 and 4 to 6, an elastic film 30 is stacked between the first sheet layer 20A and the second sheet layer 20B, and as illustrated in FIG. 7, the outer member 20 has an elastic film stretchable structure 20X in which the first sheet layer 20A and the second sheet layer 20B are joined through the through holes 31 penetrating the elastic film 30 at a large number of sheet joined portions 40 arranged at intervals, and a stretchable direction ED is the width direction WD. The first sheet layer 20A and the second sheet layer 20B may be indirectly joined via the elastic film 30, not through the through holes 31 of the elastic film 30. The planar shape of the outer member 20 is formed by recessed leg lines 29 so as to form leg openings at both side edges in the width direction of the intermediate portion L and has a shape resembling an hourglass as a whole. The outer member 20 may be divided into the front body F and the back body B and may be arranged such that those are spaced apart from each other in the front-back direction LD at the crotch portion.

Figure 2:
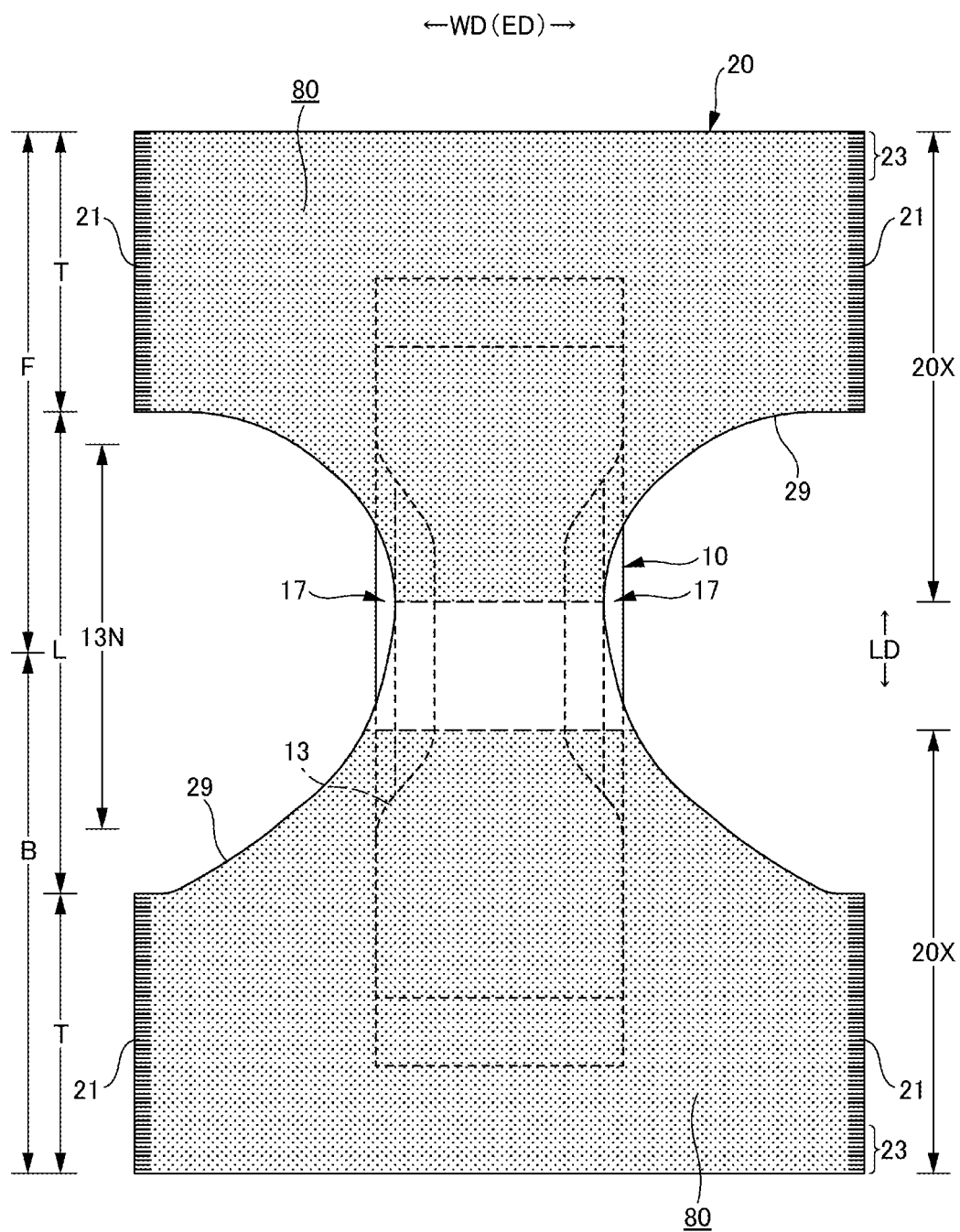
FIG. 2 is a plan view (outer surface side) of an underpants-type disposable diaper in a spread state.
Figure 3:
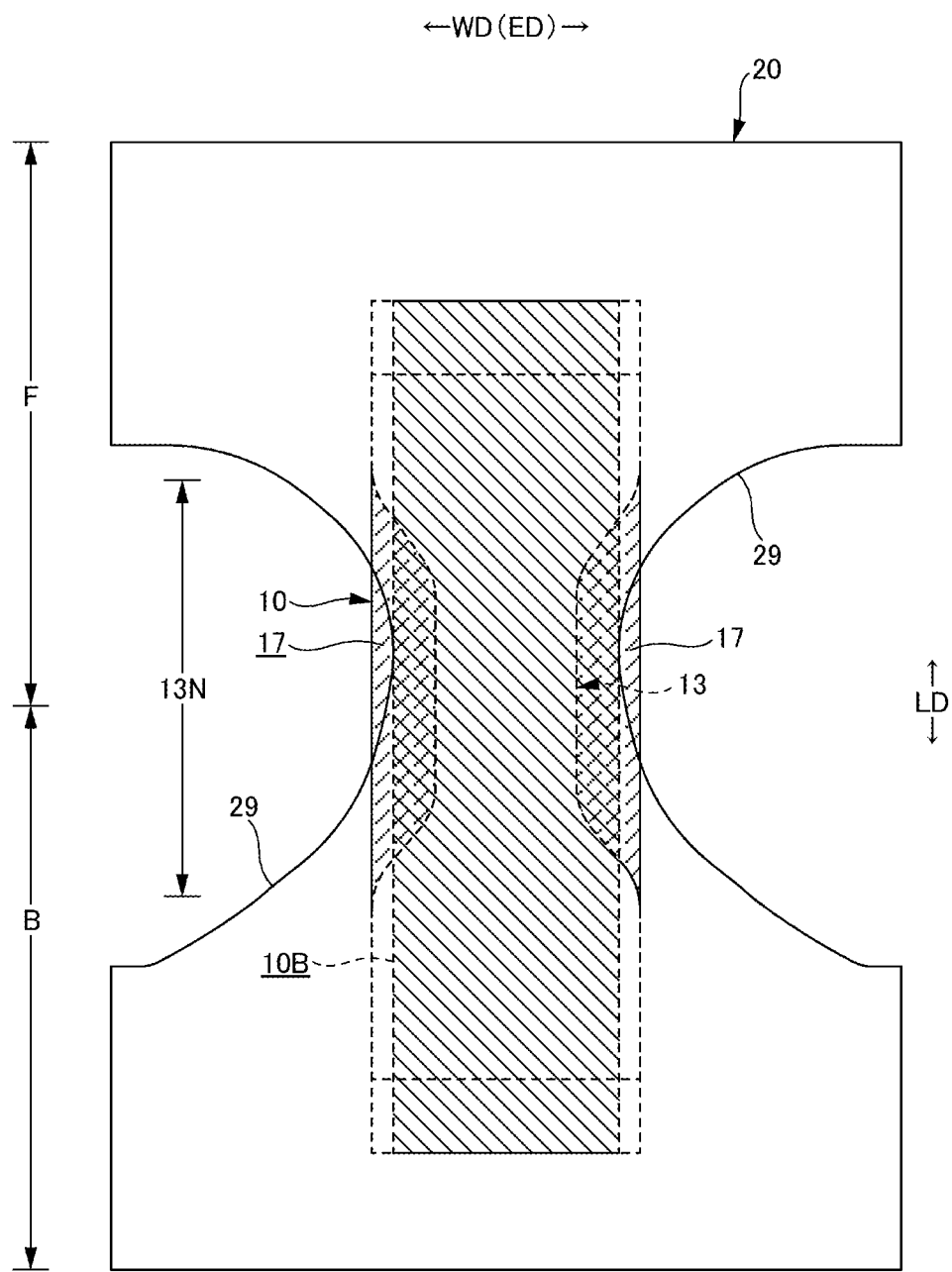
FIG. 3 is a plan view illustrating only a main part of an underpants-type disposable diaper in a spread state.

In the structure illustrated in FIGS. 1 and 2, the elastic film stretchable structure 20X extends to a waist region 23. When the elastic film stretchable structure 20X is used in the waist region 23, tightening of the waist region 23 may be insufficient. Therefore, as illustrated FIGS. 15 and 16, without providing the elastic film stretchable structure 20X in the waist region 23, a stretchable structure by conventional elongated waist portion elastic members 24 can be provided if necessary. However, elongated elastic members extending along leg openings are not provided at edge portions of the leg openings in the outer member 20. The waist portion elastic members 24 are a plurality of elongated elastic members such as rubber threads arranged at intervals in the front-back direction LD and apply a stretching force so as to tighten around the waist of a wearer. The waist portion elastic members 24 are not arranged substantially in a single bundle with a close spacing, but three or more, preferably five or more waist portion elastic members 24 are disposed at intervals of 3 to 8 mm so as to form a predetermined stretchable zone. A stretch rate at the time of fixing the waist elastic member 24 can be appropriately determined, but it can be set to about 230 to 320% in the case of normal adult use. Although a rubber thread is used for the waist portion elastic member 24 in the illustrated example, another elongated elastic member such as flat rubber or the like may be used. Although not illustrated, a general-purpose structure may be adopted in which only elongated elastic members such as rubber threads, flat rubbers, or the like are provided without disposing the elastic film stretchable structure 20X on the outer member 20.

In another structure, although not illustrated, appropriate deformation is possible such as a structure that the elastic film stretchable structure 20X is not provided in the intermediate portion L between the lower torso portion T of the front body F and the lower torso portion T of the back body B; a form that the stretchable structure 20X is continuously provided in the front-back direction LD from the inside of the lower torso portion T of the front body F to the inside of the lower torso portion T of the back body B through the intermediate portion L; or a form that the elastic film stretchable structure 20X is provided only in any one of the front body F and the back body B.

Figure 8:
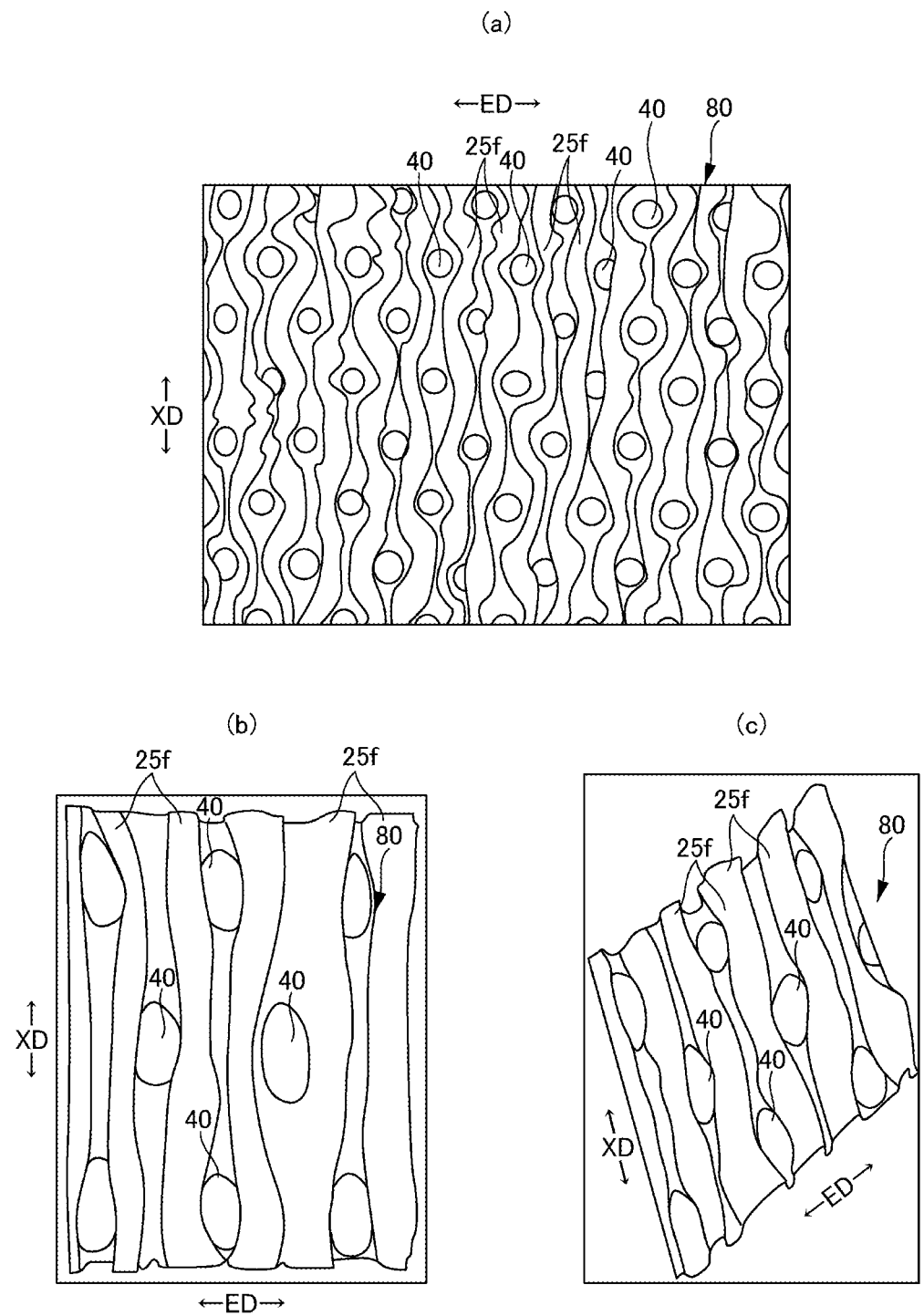
FIG. 8(a) is a trace diagram of a microscopic photograph from a planar direction.
FIG. 8(b) is a trace diagram of a high magnification micrograph photograph from a planar direction.
FIG. 8(c) is a trace diagram of a high magnification micrograph photograph from a perspective direction in a stretchable region of a sample.
Figure 9:
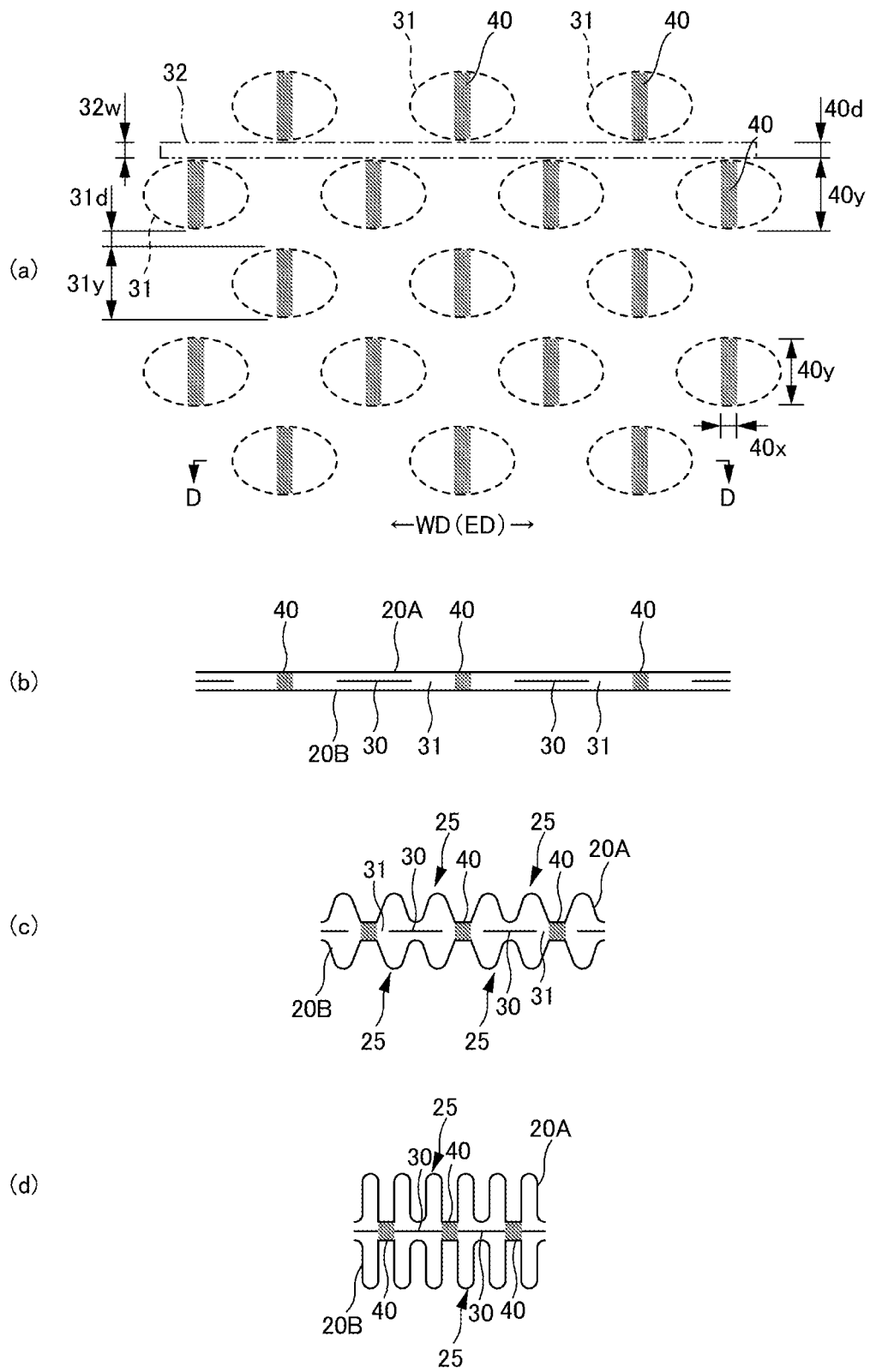
FIG. 9(a) is a plan view of a main part of a stretchable region.
FIG. 9(b) is a cross-sectional view taken along line D-D of FIG. 9(a)
FIG. 9(c) is a cross-sectional view in a worn state.
FIG. 9(d) is a cross-sectional view in a natural length state.
Figure 10:
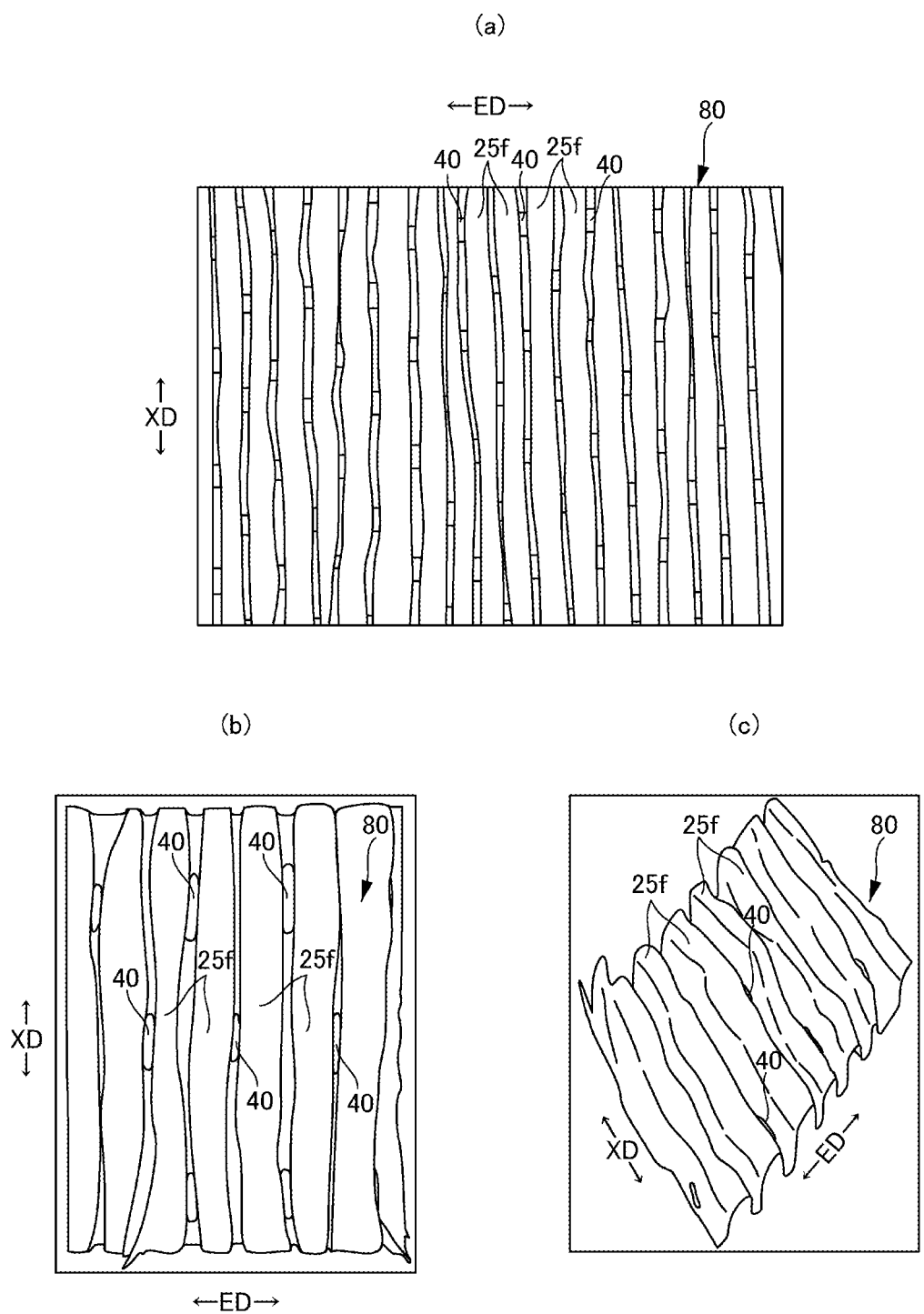
FIG. 10(a) is a trace diagram of a microscopic photograph from a planar direction.
FIG. 10(b) is a trace diagram of a high magnification micrograph from a planar direction.
FIG. 10(c) is a trace diagram of a high magnification micrograph from a perspective direction in a stretchable region of a sample.
Figure 12:
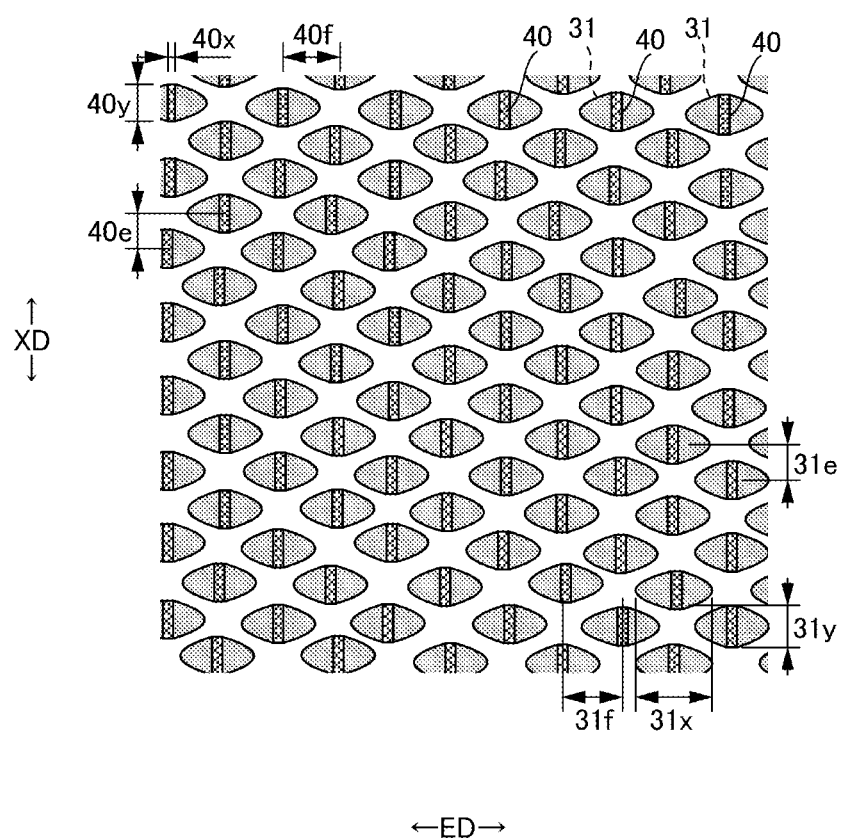
FIG. 12 is a trace diagram of a photograph of a non-stretchable region of a sample.
Figure 13:
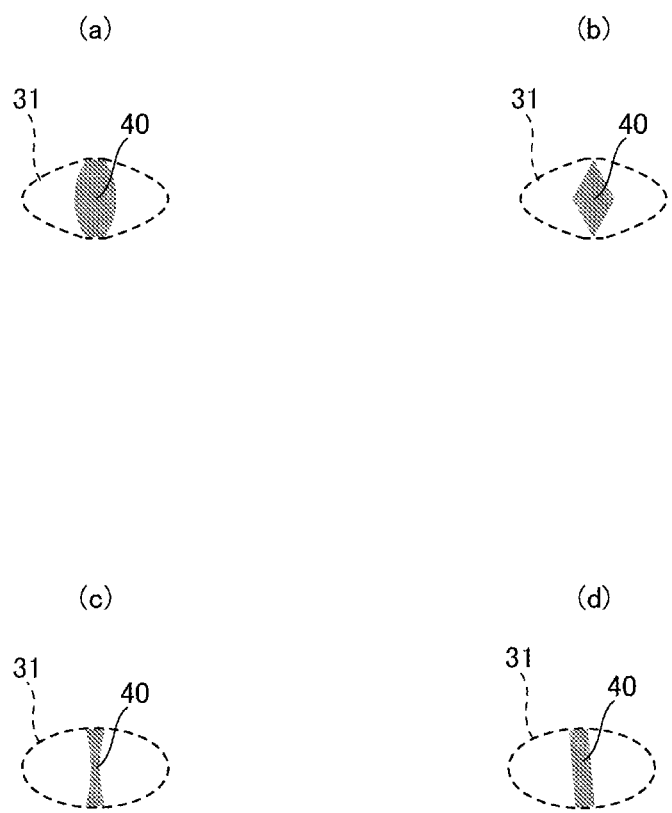
FIG. 13 is an enlarged plan view of a main part of a non-stretchable region.

Although the shape of each of the sheet joined portions 40 and the shape of each of the through holes 31 in a natural length state can be determined as appropriate, it can be an arbitrary shape such as a perfect circle (refer to FIGS. 7 and 8), an ellipse, a polygon such as a triangle, a rectangle (refer to FIGS. 9 to 12), a rhombus (refer to FIG. 13(b)), etc., a convex lens shape (refer to FIG. 13(a)), a concave lens shape (refer to FIG. 13(c)), a star shape, a cloud shape, and the like. Although the size of each of the sheet joined portions 40 is not particularly limited, the maximum length (dimension in the direction orthogonal to the stretchable direction) 40y is preferably 0.5 to 3.0 mm, particularly preferably 0.7 to 1.1 mm, and the maximum width (dimension in the extending direction) 40x is preferably 0.1 to 3.0 mm, particularly preferably 0.1 to 1.1 mm in the case where the shape is long in the direction XD orthogonal to the stretchable direction.

The size of each of the sheet joined portions 40 may be determined appropriately, but if it is too large, the hardness of the sheet joined portions 40 exerts a significant influence on the touch, and if it is too small, a joined area is small, and materials are insufficiently attached to each other. Therefore, in the usual case, the area of each sheet joined portions 40 is preferably about 0.14 to 3.5 mm$^2$. The area of an opening of each of the through holes 31 may be equal to or more than that of each of the sheet joined portions because the sheet joined portions are formed through the through holes 31, and it is preferable to set to about 1 to 1.5 times the area of each of the sheet joined portions. The area of the opening of each of the through holes 31 means a value in a natural length state and in a state where the elastic film 30, the first sheet layer 20A and the second sheet layer 20B are provided in one unit, rather than a state of the elastic film 30 alone, and means the minimum value in the case where the area of the opening of each of the through holes 31 is not uniform in the thickness direction like that the area is different between the front surface and back surface of the elastic film 30.

Figure 21:
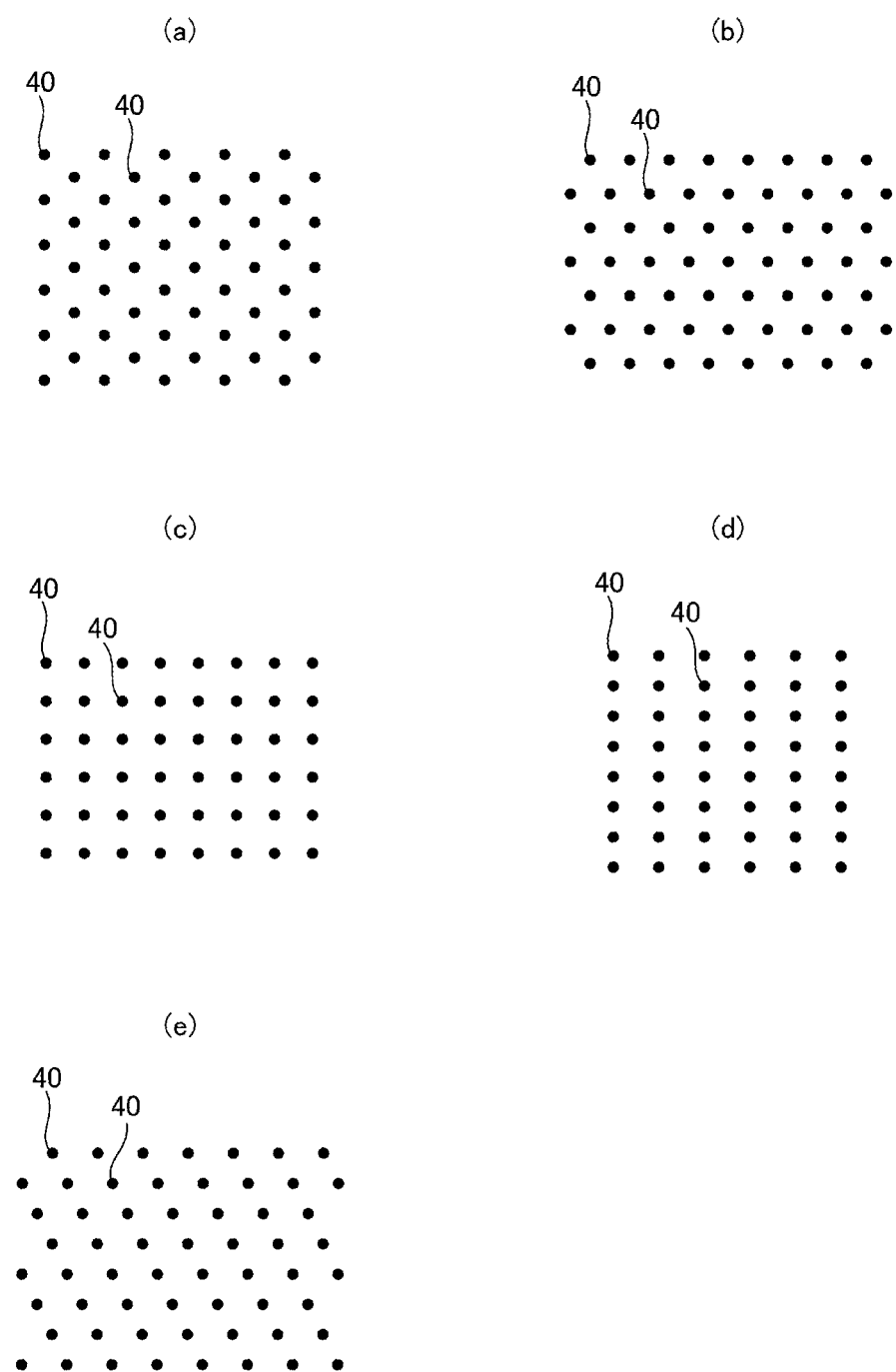
FIG. 21 is a plan view illustrating various arrangement examples of sheet joined portions.

Although the planar geometries of the sheet joined portions 40 and the through holes 31 can be appropriately determined, a planar array in which the sheet joined portions 40 and the through holes 31 are regularly repeated is preferred. In addition to the regularly repeated planar array such as an oblique lattice shape as illustrated in FIG. 21(a), a hexagonal lattice shape (these shapes are also referred to as a staggered shape) as illustrated in FIG. 21(b), a square lattice shape as illustrated in FIG. 21(c), a rectangular lattice shape as illustrated in FIG. 21(d), and a parallel lattice shape as illustrated in FIG. 21(e) (a structure in which two groups are provided such that groups each having a large number of parallel oblique direction rows intersect each other, as illustrated in the drawing), etc. (including structures in which these shapes are inclined at an angle of less than 90° with respect to the stretchable direction ED), a group of the sheet joined portions 40 (the group may be regularly or irregularly arranged, and may be a pattern or a letter shape) can be regularly repeated.

When the first sheet layer 20A and the second sheet layer 20B are joined in the sheet joined portions 40 through the through holes 31 formed in the elastic film 30, it is desirable that neither the first sheet layer 20A nor the second sheet layer 20B is joined to the elastic film 30 except at least between the first sheet layer 20A and the second sheet layer 20B in the sheet joined portions 40.

Means for joining the first sheet layer 20A and the second sheet layer 20B in the sheet joined portions 40 is not particularly limited. For example, the first sheet layer 20A and the second sheet layer 20B may be joined with a hot melt adhesive or may be joined by means of material welding such as heat sealing or ultrasonic sealing.

Figure 19:
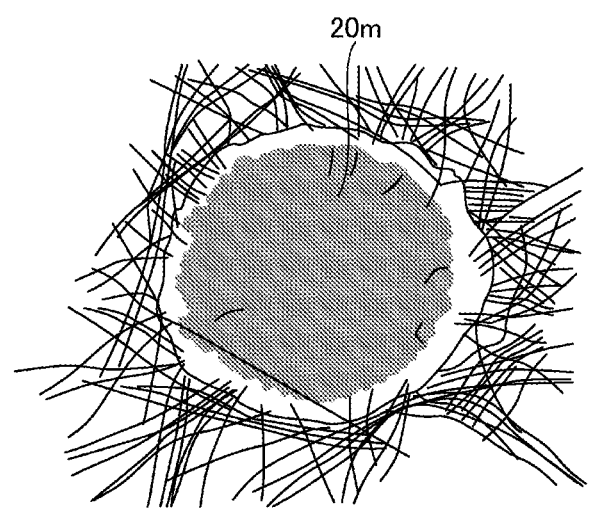
FIG. 19(a) is a trace diagram of a plan photograph of a sheet joined portion formed in a first welding mode.
FIG. 19(b) is a trace diagram of a plan photograph of a sheet joined portion formed in a third welding mode.
Figure 19:
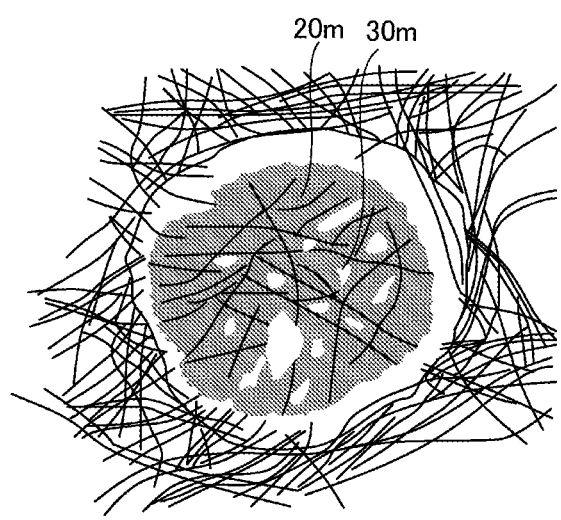

In the case where the first sheet layer 20A and the second sheet layer 20B are joined through the through holes 31 of the elastic film 30 in the sheet joined portions 40, as a mode in which the sheet joined portions 40 are formed by material welding, it is possible to adopt a first welding mode, a second welding mode, and a third welding mode. In the first welding mode, the first sheet layer 20A and the second sheet layer 20B are joined only by a melted and solidified material 20m corresponding to a most part or a part of at least one of the first sheet layer 20A and the second sheet layer 20B in the sheet joined portions 40 (refer to FIG. 17(a)). In the second welding mode, the first sheet layer 20A and the second sheet layer 20B are joined only by a melted and solidified material 30m corresponding to a whole, a most part, or a part of the elastic film 30 in the sheet joined portions 40 (refer to FIG. 17(b)). In the third welding mode, the first welding mode and the second welding mode are combined (refer to FIG. 17(c)). However, the second welding mode and the third welding mode are preferable. In particular, a mode is preferable in which the first sheet layer 20A and the second sheet layer 20B are joined by the melted and solidified material 20m of a part of the first sheet layer 20A and the second sheet layer 20B and the melted and solidified material 30m of the whole or the most part of the elastic film 30 in the sheet joined portions 40. In the third welding mode illustrated in FIG. 19(b), the melted and solidified material 30m of the elastic film 30 represented by white is found in the melted and solidified material 20m with fibers of the first sheet layer 20A or the second sheet layer 20B represented in black. However, in the first welding mode illustrated in FIG. 19(a), the melted and solidified material of the elastic film is not seen in the melted and solidified materials 20m with the fibers of the first sheet layer 20A or the second sheet layer 20B (the white part is a boundary of melted and solidified material 20m with the fibers and diffuse reflection of the melted and solidified material 20m with the fibers).

Like the first joining mode and the third joining mode, when the first sheet layer 20A and the second sheet layer 20B are joined by the melted and solidified material 20m of the most part of or a part of at least one of the first sheet layer 20A and the second sheet layer 20B as an adhesive, it is preferable that a part of the first sheet layer 20A and the second sheet layer 20B is not melted in order not to harden the sheet joined portions 40. When the first sheet layer 20A and the second sheet layer 20B are nonwoven fabrics, a case in which a part of the first sheet layer 20A and the second sheet layer 20B is not melted includes a mode in which, for all fibers of the sheet joined portions 40, the core (including not only the core of a composite fiber but also the central portion of a single component fiber) remains while the peripheral portion (including not only a sheath in a conjugate fiber but also a portion on a surface layer side of a single component fiber) is melted; and a mode in which a part of the fibers do not melt at all, while the remaining fibers melt all, or while the core remains but the surrounding portion melts in each fiber.

When the first sheet layer 20A and the second sheet layer 20B are joined using the melted and solidified material 30m of the elastic film 30 as an adhesive like the second welding mode and the third welding mode, the peel strength becomes high. In the second welding mode, under the condition that a melting point of at least one of the first sheet layer 20A and the second sheet layer 20B is higher than the melting point of the elastic film 30 and a heating temperature at the time of forming the sheet joined portions 40, the elastic film 30 is sandwiched between the first sheet layer 20A and the second sheet layer 20B, and portions to be the sheet joined portions 40 are pressurized and heated such that only the elastic film 30 is melted at the time of manufacture. On the other hand, in the third welding mode, under the condition that a melting point of at least one of the first sheet layer 20A and the second sheet layer 20B is higher than a melting point of the elastic film 30, the elastic film 30 is sandwiched between the first sheet layer 20A and the second sheet layer 20B, and portions to be the sheet joined portions 40 are pressurized and heated such that at least one of the first sheet layer 20A and the second sheet layer 20B and the elastic film 30 are melted at the time of manufacture. From such a viewpoint, the melting point of the elastic film 30 is preferably about 80 to 145° C., and the melting point of the first sheet layer 20A and the second sheet layer 20B is preferably about 85 to 190° C., particularly preferably 150 to 190° C. The difference between the melting points of the first sheet layer 20A and the second sheet layer 20B and the melting point of the elastic film 30 is preferably about 60 to 90° C. The heating temperature is preferably about 100 to 150° C.

Figure 17:
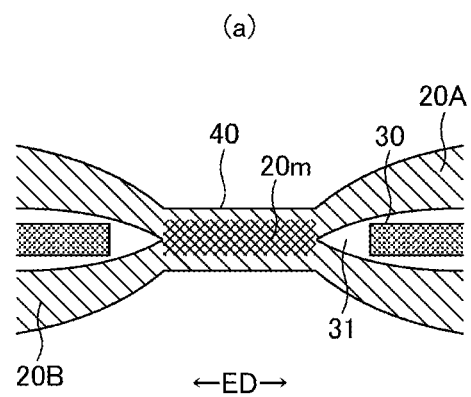
FIG. 17 is a cross-sectional view schematically illustrating a cross section of a main part of an outer member expanded to some extent.
Figure 17:
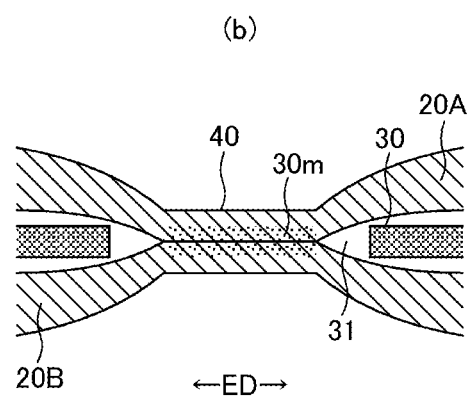
Figure 17:
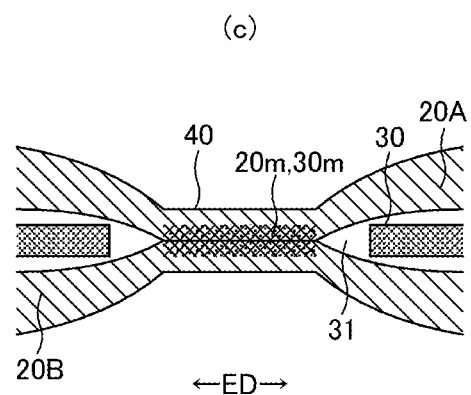
Figure 18:
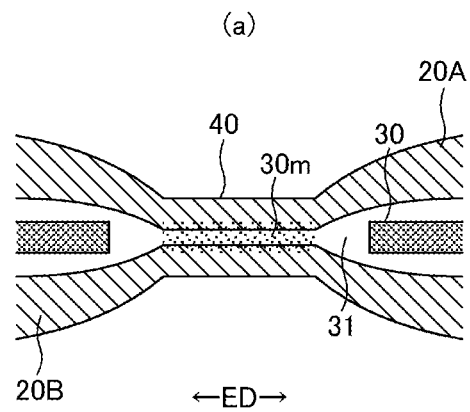
FIG. 18 is a cross-sectional view schematically illustrating a cross section of a main part of an outer member stretched to some extent.
Figure 18:
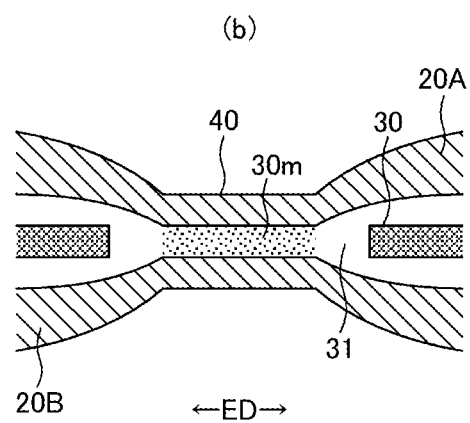
Figure 18:
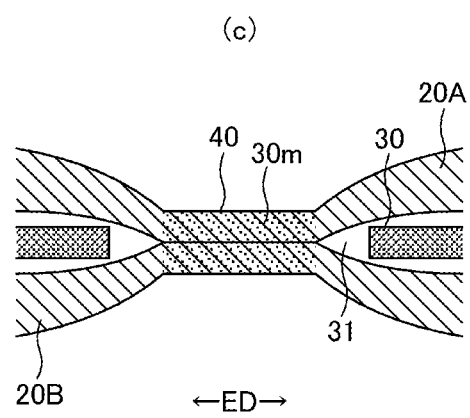

In the second welding mode and the third welding mode, when the first sheet layer 20A and the second sheet layer 20B are nonwoven fabrics, the melted and solidified material 30m of the elastic film 30 may infiltrate among the fibers throughout the entire thickness direction of the first sheet layer 20A and the second sheet layer 20B in the sheet joined portions 40 as illustrated in FIG. 18(c). However, as illustrated in FIGS. 17(b) and 17(c) and 18(a), in the mode in which the melted and solidified material 30m infiltrates among the fibers in the thickness direction halfway or in the mode in which the melted and solidified material 30m hardly filtrate among the fibers of the first sheet layer 20A and the second sheet layer 20B as illustrated in FIG. 18(b), the flexibility of the sheet joined portions 40 is further improved.

Figure 20:
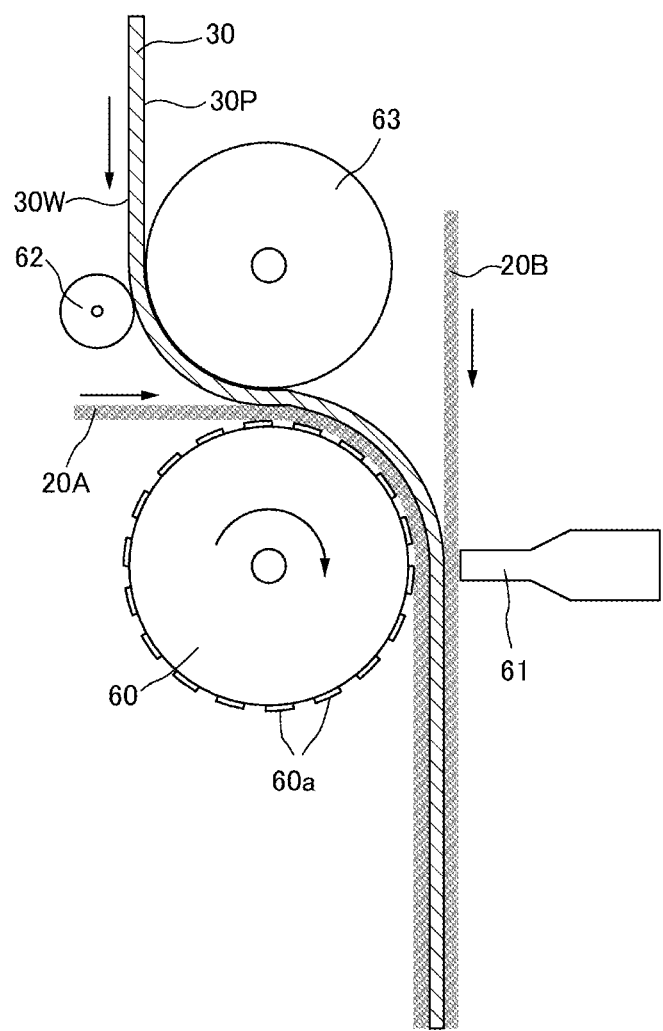
FIG. 20 is a schematic diagram of an ultrasonic sealing device.

FIG. 20 illustrates an example of an ultrasonic sealing device suitable for forming the second welding mode and the third welding mode. In this ultrasonic sealing device, to form the sheet joined portions 40, the first sheet layer 20A, the elastic film 30, and the second sheet layer 20B are fed between an ultrasonic horn 61 and an anvil roll 60 having protrusions 60a formed in a pattern of the sheet joined portions 40 on an external surface. In this instance, for example, when a feed speed of conveyance of the elastic film 30 at an upstream side by a feed drive roll 63 and a nip roll 62 is controlled to be lower than a feed speed of conveyance after the anvil roll 60 and the ultrasonic horn 61, the elastic film 30 is stretched to a predetermined stretch rate in an MD (machine direction, flow direction) on a path from a nip position by the feed drive roll 63 and the nip roll 62 to a sealing position by the anvil roll 60 and the ultrasonic horn 61. A stretch rate of the elastic film 30 may be set by selecting a speed difference between the anvil roll 60 and the feed drive roll 63, and may be set to, for example, about 300% to 500%. Reference symbol 62 denotes the nip roll. The first sheet layer 20A, the elastic film 30, and the second sheet layer 20B fed between the anvil roll 60 and the ultrasonic horn 61 are, in a stacked state in this order, heated by ultrasonic vibration energy of the ultrasonic horn 61 while being pressed between the protrusions 60a and the ultrasonic horn 61. Further, the through holes 31 are formed in the elastic film 30 by melting only the elastic film 30 or melting the elastic film 30 and at least one of the first sheet layer 20A and the second sheet layer 20B. At the same time, the first sheet layer 20A and the second sheet layer 20B are joined through the through holes 31. Therefore, in this case, an area rate of the sheet joined portions 40 may be selected by selecting a size, a shape, a separation interval, an arrangement pattern in a roll length direction and a roll circumferential direction, etc. of the protrusions 60a of the anvil roll 60.

Although the reason for formation of the through holes 31 is not necessarily clear, it is considered that openings are formed by melting the elastic film 30 at portions corresponding to the protrusions 60a of the anvil roll 60 so as to be removed from the surroundings. In this instance, a portion between the two adjacent through holes 31 arranged in the stretchable direction in the elastic film 30 is cut at both sides thereof in the stretchable direction by the through holes 31 as illustrated in FIG. 7(a), FIG. 9(a), and FIG. 11(a), and supports at both sides in a contraction direction are lost. Thus, within an extent that continuity in a direction orthogonal to the contraction direction can be maintained, the closer to the central side of the direction orthogonal to the stretchable direction, the more the elastic film 30 contracts to the central side in the stretchable direction to be commensurable so that the through holes 31 are enlarged in the stretchable direction. When the sheet joined portions 40 are formed in a pattern with sections being left in which the elastic film 30 linearly continues along the stretchable direction, as illustrated in FIG. 7(a) and FIG. 9(a), as in a stretchable region 80 described below, and when the elastic film 30 contracts to the natural length state for example by cutting for obtaining individual products, enlarged portions of each through hole 31 contract in the stretchable direction so that gaps cannot be formed between each through hole 31 and each sheet joined portion 40. On the other hand, when the sheet joined portions 40 are formed in a pattern without such sections in which the elastic film 30 linearly continues along the stretchable direction, as in a non-stretchable region 70 described below, as illustrated in FIG. 11(a), even if the elastic film 30 is cut for obtaining the individual products, contraction is not substantially performed. Thus, large gaps are left between each through hole 31 and each sheet joined portion 40.

The constituent materials of the first sheet layer 20A and the second sheet layer 20B are not particularly limited as long as they are in the form of a sheet, but it is preferable to use a nonwoven fabric from the viewpoints of air permeability and flexibility. In the nonwoven fabric, a material fiber thereof is not particularly limited. Examples of the nonwoven fabric can include synthetic fibers such as olefin type such as polyethylene and polypropylene, polyester type, and polyamide type, regenerated fibers such as rayon and cupra, natural fibers such as cotton, mixed and composite fibers in which two or more of these are used. Further, the nonwoven fabric may be manufactured by any processing. Examples of the processing method include known methods such as a spun lace method, a spunbond method, a thermal bond method, a melt blown method, a needle punch method, an air-through method, and a point bond method. When a nonwoven fabric is used, its basis weight is preferably about 12 to 20 g/m$^2$. Further, a part or the whole of the first sheet layer 20A and the second sheet layer 20B may be a pair of layers in which a single material is folded back to face each other. For example, as in the illustrated embodiment, in the waist region 23, the constituent material located on the outer side is the second sheet layer 20B, and the folded portion 20C folded back to the inner surface side at a waist opening edge is the first sheet layer 20A, and an elastic film 30 is interposed therebetween. In the rest part, the constituent material located on the inner side is the first sheet layer 20A, the constituent material located on the outer side is the second sheet layer 20B, and the elastic film 30 can be interposed therebetween. It is obvious that the constituent material of the first sheet layer 20A and the constituent material of the second sheet layer 20B can be individually provided throughout the entire front-back direction LD, and without folding back the constituent materials, the elastic film 30 may be interposed between the constituent material of the first sheet layer 20A and the constituent material of the second sheet layer 20B.

The elastic film 30 may be composed of any thermoplastic resin film having elasticity. For example, it is possible to use a film in which a large number of holes or slits are formed for ventilation in addition to a non-perforate film. In particular, it is preferable when the elastic film 30 has a tensile strength in the width direction WD (the stretchable direction, the MD) of 8 to 25 N/35 mm, tensile strength in the front-back direction LD (the direction orthogonal to the stretchable direction, the CD (cross direction)) of 5 to 20 N/35 mm, tensile elongation in the width direction WD of 450 to 1,050%, and tensile elongation in the front-back direction LD of 450 to 1,400%. The thickness of the elastic film 30 is not particularly restricted. However, the thickness is preferably in a range of about 20 to 40 μm.

(Stretchable Region)

A region having the elastic film stretchable structure 20X in the outer member 20 has a stretchable region which is stretchable in the width direction WD. The stretchable region 80 has sections 32 in which the elastic film 30 linearly continues along the width direction WD. The stretchable region contracted in the width direction WD by a contraction force of the elastic film 30 is extensible in the width direction WD. More specifically, in a state in which the elastic film 30 is stretched in the width direction WD, the first sheet layer 20A and the second sheet layer 20B are joined through the through holes 31 of the elastic film 30 at intervals in the width direction WD and the front-back direction LD orthogonal thereto (direction XD orthogonal to the stretchable direction), and the large number of sheet joined portions 40 are formed, thereby forming the elastic film stretchable structure 20X. Further, in the stretchable region 80, it is possible to impart elasticity by arranging the through holes 31 such that the stretchable region 80 has the sections in which the elastic film 30 linearly continues along the width direction WD.

In the stretchable region 80, in the natural length state, as illustrated in FIG. 7(d) and FIG. 9(d), the first sheet layer 20A and the second sheet layer 20B between the two adjacent sheet joined portions 40 are raised in directions away from each other, and thus a contraction wrinkle 25 extending in the front-back direction LD is formed. Further, as illustrated in FIG. 7(c) and FIG. 9(c), even in a worn state stretched to some extent in the width direction WD, the contraction wrinkles 25 are still remained while being stretched. In addition, as in the illustrated mode, when neither the first sheet layer 20A nor the second sheet layer 20B is joined to the elastic film 30 except at least between the first sheet layer 20A and the second sheet layer 20B in the sheet joined portions 40, as is understood from FIG. 7(c) and FIG. 9(c) assuming the worn state and FIGS. 7(a) and 7(b) and FIGS. 9(a) and 9(b) assuming the spread state of the first sheet layer 20A and the second sheet layer 20B, the gaps are formed between each through hole 31 of the elastic film 30 and each sheet joined portion 40 and in these states, air permeability is imparted by these gaps even when the material of the elastic film 30 is a non-perforate film or a non-perforate sheet. In addition, in the natural length state illustrated in FIG. 7(d) and FIG. 9(d), the through holes 31 are narrowed due to contraction of the elastic film 30, and the gaps are hardly formed between the through hole 31 and the sheet joined portion 40. States of the contraction wrinkle 25 in the worn state and the natural length state are shown in also FIG. 8 and FIG. 10.

It is desirable that an elongation at an elastic limit of the stretchable region 80 in the width direction WD is set to 200% or more (preferably 265% to 295%). The elongation at the elastic limit of the stretchable region 80 is substantially determined by the stretch rate of the elastic film 30 in the manufacturing. Further based on this, the elongation at the elastic limit decreases due to a factor that inhibits contraction in the width direction WD. A main inhibition factor corresponds to a ratio of the length 40x of the sheet joined portions 40 to a unit length in the width direction WD. As this ratio increases, the elongation at the elastic limit decreases. In general, since the length 40x of each of the sheet joined portions 40 correlates with the area rate of the sheet joined portions 40, the elongation at the elastic limit of the stretchable region 80 may be adjusted by the area rate of the sheet joined portions 40.

Stretching stress of the stretchable region 80 may be adjusted mainly by a sum of widths 32w of the sections 32 in which the elastic film 30 linearly continues along the width direction WD. The width 32w of the section 32 in which the elastic film 30 linearly continues along the width direction WD is equal to an interval 31d of the through holes 31 in the front-back direction LD coming into contact with both side edges of the continuing section 32. The interval 31d of the through holes 31 is equal to an interval 40d of the sheet joined portions 40 in the front-back direction LD coming into contact with the both side edges of the continuing section in the front-back direction LD, when the length 31y of the through hole 31 in the front-back direction LD is equal to the length 40y of the sheet joined portion 40 in the front-back direction LD (for example, when a scheme of simultaneously forming the through holes 31 and the sheet joined portions 40 described above is adopted). Therefore, in this case, the stretching stress of the stretchable region 80 may be adjusted by a ratio of the length 40y of each of the sheet joined portions 40 to a unit length in the front-back direction LD. In general, since the length 40y of each of the sheet joined portions 40 correlates with the area rate of the sheet joined portions 40, the stretching stress of the stretchable region 80 may be adjusted by the area rate of the sheet joined portions 40. The stretching stress in stretching to 50% of an elastic limit may be estimated as the stretching stress of the stretchable region 80.

The area rate of the sheet joined portions 40 and the area of each of the sheet joined portions 40 in the stretchable region 80 may be appropriately determined. However, in general, the area rate and the areas are preferably set within the following ranges.

Area of each of sheet joined portions 40: 0.14 to 3.5 mm² (particularly 0.14 to 1.0 mm²)

Area rate of sheet joined portions 40: 1.8 to 19.1% (particularly 1.8 to 10.6%)

Figure 15:
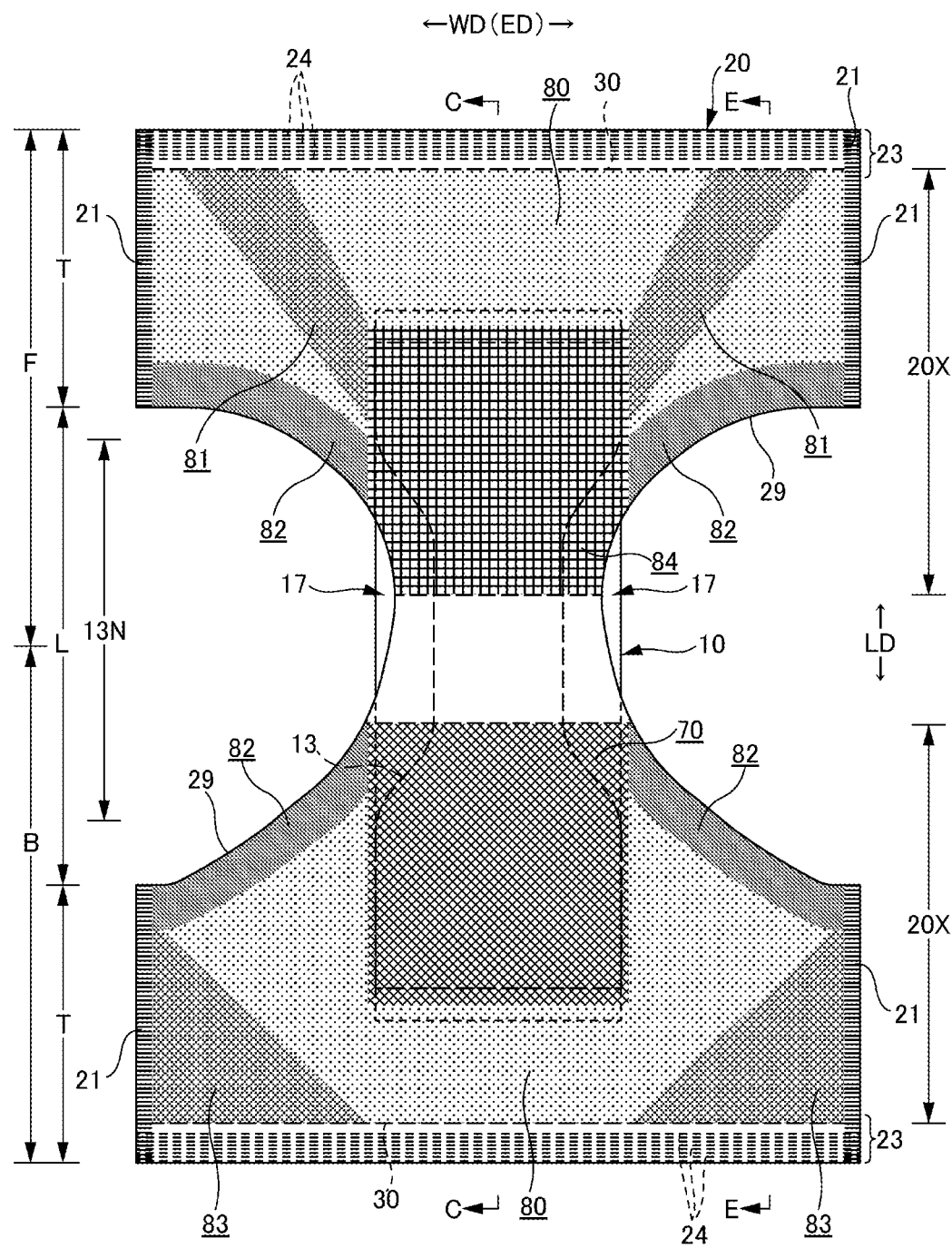
FIG. 15 is a plan view (outer surface side) of an underpants-type disposable diaper in a spread state.
Figure 16:
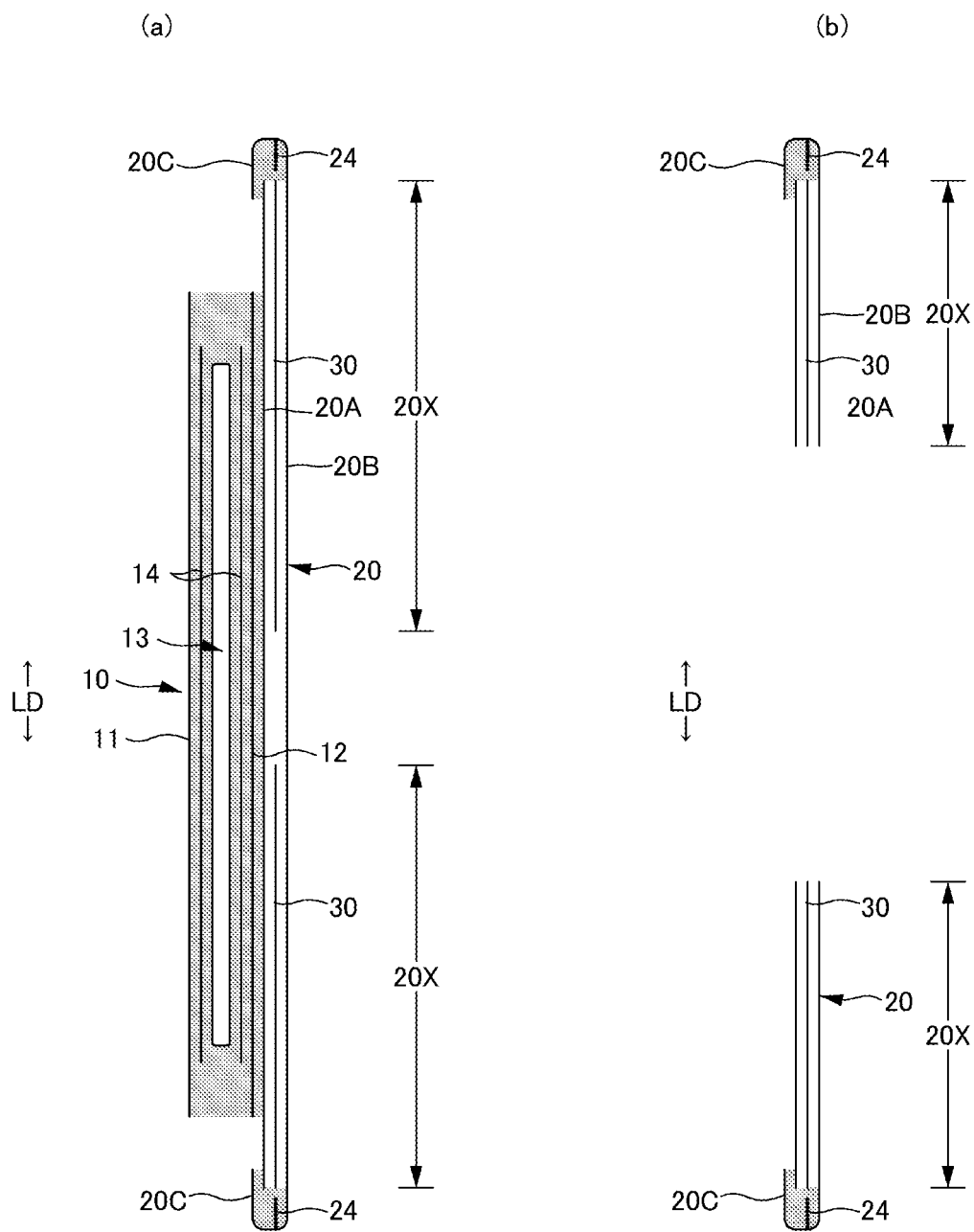
FIG. 16(a) is a cross sectional view taken along line C-C of FIG. 15.
FIG. 16(b) is a cross sectional view taken along line E-E of FIG. 15.

As described above, the elongation at the elastic limit and the stretching stress of the stretchable region 80 may be adjusted by the area of each of the sheet joined portions 40. Thus, as illustrated in FIG. 15, it is possible to provide a plurality of regions having different area rates of the sheet joined portions 40 in the stretchable region 80, and to change fitting depending on the sites. In the embodiment illustrated in FIG. 15, in the front body F, regions 81, each of which is extending in an oblique direction along a groin and edge portion regions 82 of the leg openings, have, when compared to other regions, higher area rates of the sheet joined portions 40, and thus have smaller stretching stresses, resulting in abilities to stretch flexibly. In addition, in the back body B, ilium facing regions 83 and the edge portion regions 82 of the leg openings have, when compared to other regions, higher area rates of the sheet joined portions 40, and thus have smaller stretching stresses, resulting in abilities to stretch flexibly.

(Non-Stretchable Region)

In a region having the elastic film stretchable structure 20X in the outer member 20, as illustrated in FIG. 15, it is possible to provide the non-stretchable region 70 on at least one side of the stretchable region 80 in the width direction. Arrangement of the stretchable region 80 and the non-stretchable region 70 may be appropriately determined. In the case of the outer member 20 of the underpants-type disposable diaper in the present embodiment, a portion overlapping with the absorber 13 is a region unnecessary to stretch and contract. Thus, as in the illustrated embodiment, a part or a whole of the portion overlapping with the absorber 13 (it is desirable to include substantially the entire inner and outer joined region 10B) is preferably set to the non-stretchable region 70. It is as a matter of course possible to provide the non-stretchable region 70 with a range beyond the region overlapping with the absorber 13 to a region not overlapping with the absorber 13 located adjacent to the non-stretchable region 70 in the width direction or the front-back direction thereof, or it is possible to provide the non-stretchable region 70 only in the region not overlapping with the absorber 13.

Figure 11:
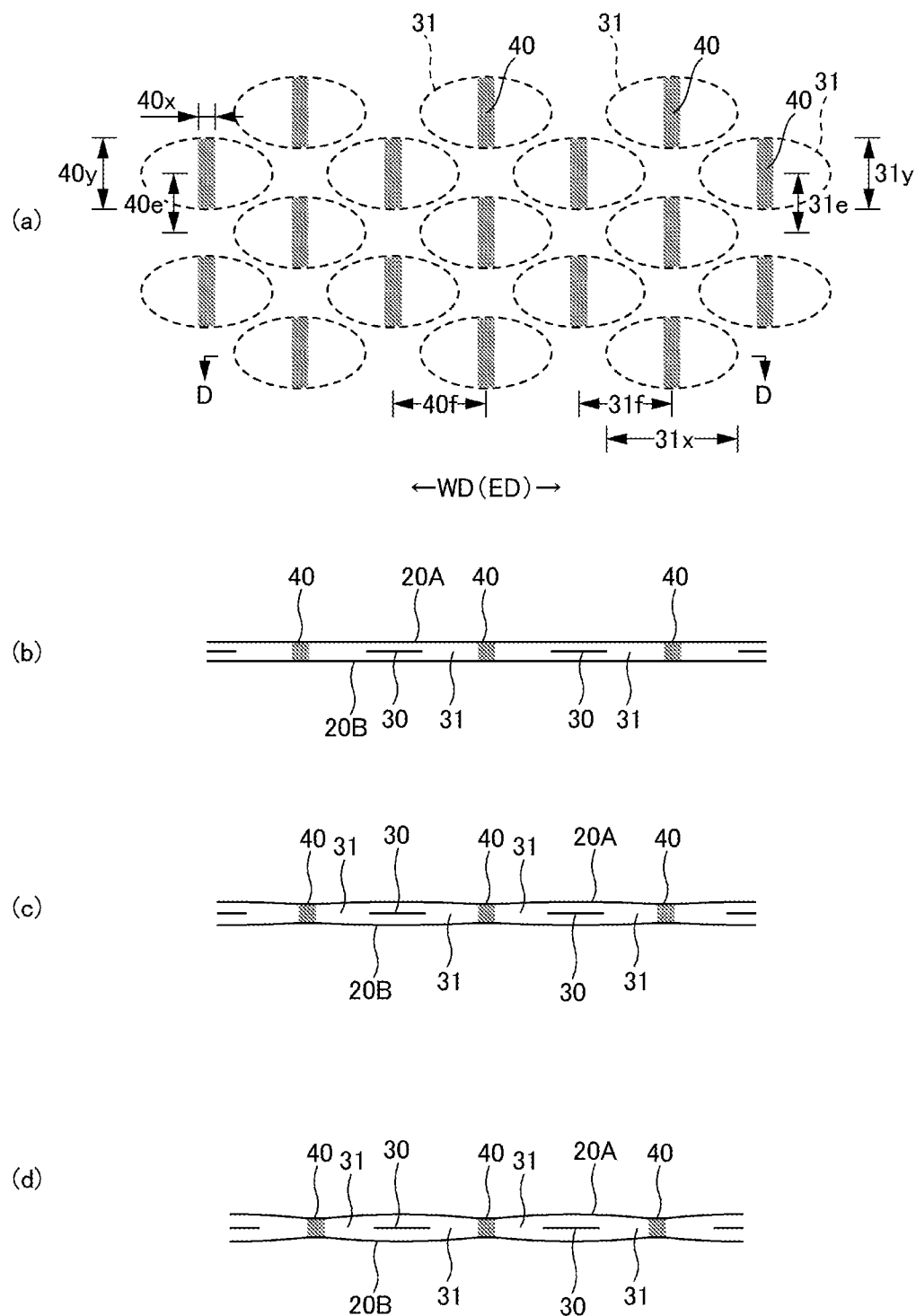
FIG. 11(a) is a plan view of a main part of a non-stretchable region.
FIG. 11(b) is a cross-sectional view taken along line D-D of FIG. 11(a)
FIG. 11(c) is a cross-sectional view in a worn state.
FIG. 11(d) is a cross-sectional view in a natural length state.

The non-stretchable region 70 is configured, even though the elastic film 30 continues in the width direction WD, so as not to have a section in which the elastic film 30 linearly continues along the width direction WD, due to the presence of the through holes 31. Therefore, even though the elastic film stretchable structure 20X is configured as a whole to include both the stretchable region 80 and the non-stretchable region 70 by joining the first sheet layer 20A and the second sheet layer 20B through the through holes 31 of the elastic film 30 to form the large number of sheet joined portions 40 at intervals in the width direction WD and the front-back direction LD orthogonal thereto while the elastic film 30 is stretched in the width direction WD, in the non-stretchable region 70, the elastic film 30 does not linearly continue along the width direction as illustrated in FIG. 11. Thus, the contraction force of the elastic film 30 hardly acts on the first sheet layer 20A and the second sheet layer 20B, elasticity is almost lost, and the elongation at the elastic limit approaches 100%. Further, in the non-stretchable region 70, the first sheet layer 20A and the second sheet layer 20B are joined by the large number of sheet joined portions 40 arranged at intervals, and the sheet joined portions 40 are discontinuous. Thus, a decrease in flexibility is prevented. In other words, it is possible to form the stretchable region 80 and the non-stretchable region 70 depending on the presence or absence of the section in which the elastic film 30 does not linearly continue along the width direction. In addition, continuity of the elastic film 30 still remains in the non-stretchable region 70. As understood from FIG. 12, since an independent cut piece of the elastic film 30 is not left, and no wrinkle is formed, appearance is extremely excellent, and air permeability in the thickness direction by the through holes 31 is ensured. In the non-stretchable region 70, the elongation at the elastic limit in the width direction WD is preferably 120% or less (preferably 110% or less, more preferably 100%).

An arrangement pattern of the through holes 31 in the elastic film 30 in the non-stretchable region 70 may be appropriately determined. However, when staggered arrangement is adopted as illustrated in FIG. 11, and a pattern in which a center-to-center interval 31$e$ of the through holes 31 in the front-back direction LD is shorter than the length 31$y$ of each of the through holes 31 in the front-back direction LD is adopted, linear continuity in the width direction WD may be almost completely eliminated while maintaining continuity of the elastic film 30, and appearance is preferable as illustrated in FIG. 12. In this case, it is more preferable that a center-to-center interval 31$f$ of the through holes 31 in the width direction WD is shorter than a length 31$x$ of each of the through holes 31 in the width direction WD.

In general, especially when stretching stress is in a range of 4 to 12 N/35 mm in stretching the elastic film 30 four times in the width direction, in a state in which the non-stretchable region 70 is stretched to the elastic limit in the width direction, the center-to-center interval 31$e$ of the through holes 31 in the front-back direction LD is preferably in a range of 0.4 to 2.7 mm, and the length 31$y$ of each of the through holes 31 in the front-back direction LD is preferably in a range of 0.5 to 3.0 mm, particularly in a range of 0.7 to 1.1 mm. In addition, the center-to-center interval 31$f$ of the through holes 31 in the width direction WD is preferably 0.5 to 2 times, particularly 1 to 1.2 times the length 31$y$ of the through holes 31 in the front-back direction, and the length 31$x$ of each of the through holes 31 in the width direction WD is preferably 1.1 to 1.8 times, particularly 1.1 to 1.4 times the center-to-center interval 31$f$ of the through holes 31 in the width direction. In a state in which the non-stretchable region 70 is stretched to an elastic limit in the width direction WD (in other words, in a state in which the first sheet layer 20A and the second sheet layer 20B are completely spread), the center-to-center interval 31$f$ of the through holes 31 in the width direction WD is equal to a center-to-center interval 40$f$ of the sheet joined portions 40 in the width direction WD, the center-to-center interval 31$e$ of the through holes 31 in the front-back direction is equal to a center-to-center interval 40$e$ of the sheet joined portions 40 in the front-back direction LD, and the length 31$y$ of each of the through holes 31 in the front-back direction LD is equal to the length 40$y$ of each of the sheet joined portions 40 in the front-back direction.

In a case in which neither the first sheet layer 20A nor the second sheet layer 20B is joined to the elastic film 30 except between the first sheet layer 20A and the second sheet layer 20B in the sheet joined portions 40 in the non-stretchable region 70, and the gaps, which are generated by the peripheral edge of each of the through holes 31 of the elastic film 30 and each of the sheet joined portions 40 separated from each other, are included at both sides of each of the sheet joined portions 40 in the width direction in the natural length state, air permeability is imparted at all times due to the gaps even if the material of the elastic film 30 is a non-perforate film or a non-perforate sheet, and thus such a case is preferable. In the case of adopting a scheme of simultaneously forming the through holes 31 and the sheet joined portions 40 described above, this state is automatically obtained irrespective of a shape of the sheet joined portions 40, etc.

The shape of each of the sheet joined portions 40 and the through holes 31 in the natural length state is not particularly restricted. However, it is desirable to have a small area from a viewpoint of flexibility, and it is desirable to have a shape which is long in the front-back direction LD to eliminate linear continuity in the width direction WD of the elastic film 30. Thus, it is preferable to adopt an ellipse which is long in the front-back direction LD, a rectangle (see FIG. 11 and FIG. 13(d)), the rhombus (see FIG. 13(b)), the convex lens shape (see FIG. 13(a)), and the concave lens shape (see FIG. 13(c)). However, when corners are acute as in the rhombus, the elastic film 30 is easily fractured. In contrast, the convex lens shape is preferable since welding of the sheet joined portions 40 is stabilized, and the concave lens shape is preferable in that an area may be further reduced.

It is possible to appropriately determine the area rate of the sheet joined portions 40 and the area of each of the sheet joined portions 40 in the non-stretchable region. However, in general, ranges below are preferable since the area of each of the sheet joined portions 40 is small, the area rate of the sheet joined portions 40 is low, and thus the non-stretchable region 70 is not hardened.

Area of each of sheet joined portions 40: 0.10 to 0.75 mm$^2$ (particularly 0.10 to 0.35 mm$^2$)

Area rate of sheet joined portions 40: 4 to 13% (particularly 5 to 10%)

As described above, the elongation at the elastic limit of the non-stretchable region 70 may be changed by the arrangement pattern of the through holes 31, dimensions of each of the through holes 31, and the center-to-center interval of the through holes 31. Therefore, although not illustrated, it is possible to make the elongation at the elastic limit different between a plurality of positions in the stretchable region 80 or a plurality of non-stretchable regions 70. For example, in a preferable structure, the elongation at the elastic limit in the non-stretchable region 70 of the front body F is set to be larger than the elongation at the elastic limit in the non-stretchable region 70 of the back body B.

Even though the non-stretchable region 70 has a section that linearly continues along the width direction WD similarly to the stretchable region, since the area rate of the sheet joined portions in the non-stretchable region 70 is higher than that in the stretchable region, the elongation at the elastic limit is remarkable in the non-stretchable region 70. Specifically, it is possible to adopt structures for eliminating elasticity such as a structure in which the elongation at the elastic limit is 130% or less; and a structure in which cutting is performed in the width direction at one position or a plurality of positions as in a conventional stretchable structure using a rubber thread, etc.

<Description of Terms in Specification>

The terms used in the specification have the following meanings unless otherwise stated.

The "front body" and the "back body" refer to front and back portions using the center of the underpants-type disposable diaper in the front-back direction as a boundary. In addition, the crotch portion refers to a range in the front-back direction including the center of the underpants-type disposable diaper in the front-back direction, and refers to a range in the front-back direction of a portion having a narrower part when the absorber has the narrower part.

The "elongation at the elastic limit" refers to an elongation at an elastic limit in the stretchable direction (in other words, a state in which the first sheet layer and the second sheet layer are completely spread), and expresses a length at the time of the elastic limit as a percentage when the natural length is set to 100%.

The "area rate" refers to a rate of a target portion to a unit area, and expresses the rate as a percentage by dividing a total area of the target portions (for example, the sheet joined portions 40, the openings of the through holes 31, and the vent hole) in a target region (for example, the stretchable region 80, the non-stretchable region 70, a main stretchable portion, and a damping elastic portion) by an area of the target region. Particularly, an "area rate" in a region having a stretchable structure refers to an area rate in a state of being stretched in the stretchable direction to the elastic limit. In a mode in which a large number of target portions are provided at intervals, it is desirable to obtain the area rate by using the target region of a size including ten or more target portions.

The "stretch rate" represents a value relative to the natural length (100%)

The "basis weight" is determined as follows: After the sample or test piece is preliminarily dried, it is allowed to stand in a test room or apparatus under normal conditions (the test location is at a temperature: 20±5° C., relative humidity: 65% or less) until the constant mass. The preliminary drying is to make the sample or test piece be constant mass in an environment within a relative humidity of 10 to 25% and at a temperature not exceeding 50° C. The fibers of an official moisture regain of 0.0% does not need preliminary drying. A cut sample with a size of 200 mm by 250 mm (±2 mm) is cut from the test piece in the constant mass, with a cutting template (200 mm by 250 mm, ±2 mm). The sample is weighed and the weight is multiplied by 20 into the weight per square meter. The resulting value is defined as the basis weight.

The "thickness" of the absorber is measured using a thickness measurement apparatus of OZAKI MGF Co., Ltd. (PEACOCK, Dial Thickness Gauge Large Type, Model J-B (Measurement Range 0 to 35 mm) or Model K-4 (Measurement Range 0 to 50 mm)) by horizontally disposing a sample and the thickness measurement apparatus.

A "thickness" other than the above-described thickness is automatically determined with an automatic thickness gauge (KES-G5 handy compression measurement program) under the conditions of a load of 10 gf/cm$^2$ and a pressurization area of 2 cm$^2$.

The "tensile strength" and the "tensile elongation (elongation at break)" are measured at an initial chuck interval of 50 mm and a speed of testing of 300 mm/min with a tensile tester (for example, AUTOGRAPH AGS-G100N available from SHIMADZU) in accordance with JIS K7127:1999 "Plastics—Determination of tensile properties", except that the test piece is a rectangle with a width of 35 mm and a length of 80 mm.

The "stretching stress" indicates the tensile stress (N/35 mm) when the sample is stretched in an elastic region that is measured by a tensile test at an initial chuck interval (distance between marked lines) of 50 mm and a speed of testing of 300 mm/min in accordance with JIS K7127:1999 "Plastic—Determination of tensile properties", and an extent of stretching may be appropriately determined depending on the test object. A test piece is preferably formed in a rectangular shape having a width of 35 mm and a length of 80 mm or more. If a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress. For example, AUTOGRAPH AGS-G100N manufactured by SHIMADZU may be used as a tensile tester.

The "spread state" refers to a flatly spread state without contraction or slack.

Unless otherwise specified, dimensions of each portion refer to dimensions in the spread state, not the natural length state.

In the absence of description about an environmental condition in a test or measurement, the test or measurement is performed in a test room or apparatus under normal conditions (the test location is at a temperature 20±5° C., relative humidity 65% or less).

INDUSTRIAL APPLICABILITY

The present invention is applicable to an underpants-type disposable diaper as in the above example.

REFERENCE SIGNS LIST 10 inner member
10B inner and outer joined region
11 liquid pervious top sheet
12 liquid impervious sheet
13 absorber
13N narrowing portion
14 package sheet
17 non absorber side part
20 outer member
20A first sheet layer
20B second sheet layer
20C folded back portion
20X elastic film stretchable structure
21 side seal portion
23 waist region
24 waist elastic member
25 contraction wrinkle
29 leg line
30 elastic film
31 through hole
40 sheet joined portion
70 non-stretchable region
80 stretchable region
90 three-dimensional gather
93 fallen portion
94 free portion
95 gather sheet
95t surface layer
96 gather elastic member
97 fallen non-stretchable portion
98 character representation
B back body
ED stretchable direction
F front body
L intermediate portion
LD front-back direction
T lower torso portion
WD width direction

The invention claimed is:

1. An underpants-type disposable diaper comprising: an outer member, which is extending from a front body to a back body as one unit, or outer members, which are separately provided on the front body and the back body; an inner member, which has a liquid pervious top sheet positioned on a front surface side, a liquid impervious sheet positioned on a back surface side, and an absorber interposed therebetween, which extends in the front-back direction from the front body to the back body, and which is joined to the outer member; and three-dimensional gathers, which are provided on both sides in the width direction of the inner member,
wherein each of the three-dimensional gathers includes a main unit section positioned on each of both side portions of the inner member, fallen portions located on the front and back end portions of the main unit section and fixed in a fallen state, a non-fixed free portion located between the fallen portions in the main unit section, and a gather elastic member attached to the free portion, such that the free portion stands up by a contraction force of the gather elastic member,
wherein the fallen portion has a fallen non-stretchable portion to which the contraction force of the gather elastic member does not act,
wherein a character representation is printed at a position in the fallen non-stretchable portion of the inner member, and the character representation is made visible on the inside of the diaper, and
wherein the fallen non-stretchable portion comprises a surface layer located on a most front surface side and a back surface layer adjacent to a back surface side of the surface layer, the surface layer is not fixed to the back surface layer, and the character representation is printed on the surface layer.

2. The underpants-type disposable diaper according to claim 1,
wherein the outer member has a stretchable region, which is stretchable in the width direction, at a position corresponding to the character representation in the front-back direction, and
each of both side portions of the inner member in the width direction including at least a part of the character representation is not joined to the outer member.

3. The underpants-type disposable diaper according to claim 2,
wherein the absorber extends in the front-back direction so as not to reach a position of the fallen portion at a front side and a position of the fallen portion at a back side,
the liquid impervious sheet extends in the front-back direction so as to reach the position of the fallen portion at the front side and the position of the fallen portion at the back side, and the liquid impervious sheet is provided so as to include at least a position of the character representation in the fallen portion.

4. The underpants-type disposable diaper according to claim 2,
wherein the character representation is printed on a surface located on the most front surface side of the surface layer.

5. The underpants-type disposable diaper according to claim 2,
wherein the character representation is printed on a surface located on the back surface side of the surface layer.

6. The underpants-type disposable diaper according to claim 1,
wherein the absorber extends in the front-back direction so as not to reach a position of the fallen portion at a front side and a position of the fallen portion at a back side,
the liquid impervious sheet extends in the front-back direction so as to reach the position of the fallen portion at the front side and the position of the fallen portion at the back side, and
the liquid impervious sheet is provided so as to include at least a position of the character representation in the fallen portion.

7. The underpants-type disposable diaper according to claim 6,
wherein the character representation is printed on a surface located on the back surface side of the surface layer.

8. The underpants-type disposable diaper according to claim 1,
wherein the character representation is printed on a surface located on the most front surface side of the surface layer.

9. The underpants-type disposable diaper according to claim 1,
wherein the character representation is printed on a surface located on the back surface side of the surface layer.

* * * * *